United States Patent
Riva et al.

(10) Patent No.: US 9,593,127 B2
(45) Date of Patent: Mar. 14, 2017

(54) HETEROCYCLYLALKYNE DERIVATIVES AND THEIR USE AS MODULATORS OF MGLUR5 RECEPTORS

(71) Applicant: RECORDATI IRELAND LTD., Co. Cork OT (IE)

(72) Inventors: Carlo Riva, Varese (IT); Carlo De Toma, Milan (IT); Patrizia Angelico, Sesto S. Giovanni (IT); Elena Poggesi, Milan (IT); Davide Graziani, Milan (IT)

(73) Assignee: RECORDATI IRELAND LTD. (IE)

( * ) Notice: Subject to any disclaimer, the term of this patent is extended or adjusted under 35 U.S.C. 154(b) by 0 days.

(21) Appl. No.: 14/983,277

(22) Filed: Dec. 29, 2015

(65) Prior Publication Data
US 2016/0185798 A1 Jun. 30, 2016

Related U.S. Application Data

(60) Provisional application No. 62/097,482, filed on Dec. 29, 2014.

(51) Int. Cl.
C07D 498/04 (2006.01)
A61K 31/424 (2006.01)

(52) U.S. Cl.
CPC .......... *C07D 498/04* (2013.01); *A61K 31/424* (2013.01)

(58) Field of Classification Search
None
See application file for complete search history.

(56) References Cited

FOREIGN PATENT DOCUMENTS

WO 0200196 A2 1/2002

OTHER PUBLICATIONS

O'Brien et al., Mol. Pharma. (2003), vol. 64, pp. 731-740.*
Lindsley et al., J. Med. Chem. (2004), vol. 47, pp. 5825-5828.*
Anderson et al., J Pharmacol. Exp. Ther., (2002), vol. 303(3), pp. 1044-1051.
Berge, S. M. et al., Pharmaceutical salts. J. Pharm. Sci., (1977), vol. 66, pp. 1-19.
Chinchilla et al. Chem. Rev., (2007), vol. 107 (3), pp. 874-922.
Javitt et al. Am J. Psychiatry, (1991), vol. 148, pp. 1301-1308.
Lindsley et al. J. Med. Chem. (2004), Vol.47, pp. 5825-5828.
Lujan et al. Eur. J. Neurosci. (1996), vol. 8, pp. 1488-1500.
Mannaioni et al. NeuroSci., (2001), vol. 21, pp. 5925-5924.
Meltzer, H. Y. Biol. Psychiatry, (1999), vol. 46(10), pp. 1321-1327.
O'Brien et al. Mol. Pharma. (2003), vol. 64, pp. 731-740.
Riedel et al., Behav. Brain Res. (2003), vol. 140, pp. 1-47.
Rosenbrock et al., Eur. J. Pharma., (2010), vol. 639, pp. 40-46.
Schoepp et al., Neuropharma, (1999), vol. 38, pp. 1431-1476.
Brunton, L. L. et al. Eds. The Pharmacological Basis of Therapeutics, 12th Edition, McGraw-Hill (2011), 22 pages.
Chan et al. "Attenuation of ketamine-evoked behavioral responses by mGluR5 positive modulators in mice." Psychopharma. (2008), vol. 198, pp. 141-148.
Cheng et al. "Relationship between the Inhibition Constant (K1) and the Concentration of Inhibitor Which Causes 50 Percent Inhibition (I50) of an Enzymatic Reaction." Biochem Pharmacol. (1973), vol. 22, pp. 3099-3108.
Coyle et al., "Glutamate and Schizophrenia: Beyond the Dopamine Hypothesis." Cell. and Mol. Neurobiol. (2006)vol. 26, pp. 365-384.
Farber et al. "The glutamate synapse in neuropsychiatric disorders: Focus on schizophrenia and Alzheimer's disease." Prog. Brain Res. (1998). vol. 116, pp. 421-437.
International Search Report and Written Opinion for International Patent Application No. PCT/EP2015/081337 mailed on Feb. 26, 2016. 7 pages.
Kanemasa et al. "First Successful Metal Coordination Control in 1,3-Dipolar Cycloadditions. High-Rate Acceleration and Regio- and Stereocontrol of Nitrile Oxide Cycloadditions to the Magnesium Alkoxides of Allylic and Homoallylic Alcohols." J. Am. Chem. Soc. (1994), vol. 116, pp. 2324-2339.

* cited by examiner

*Primary Examiner* — Karl J Puttlitz
(74) *Attorney, Agent, or Firm* — Leason Ellis LLP

(57) ABSTRACT

This invention relates to compounds of formula I,

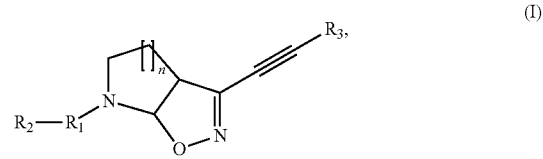

their use as allosteric modulators of mGluR5 receptor activity, pharmaceutical compositions containing the same, and methods of using the same as agents for the treatment and/or prevention of neurological and psychiatric disorders associated with glutamate dysfunction, such as schizophrenia or cognitive decline, dementia or cognitive impairment, or other pathologies that can be related directly or indirectly to glutamate dysfunction.

14 Claims, No Drawings

HETEROCYCLYLALKYNE DERIVATIVES AND THEIR USE AS MODULATORS OF MGLUR5 RECEPTORS

CROSS REFERENCE TO RELATED APPLICATIONS

This application claims priority to U.S. Provisional Patent Application Ser. No. 62/097,482, filed on Dec. 29, 2014, which is incorporated by reference in its entirety.

FIELD OF THE INVENTION

This invention relates to heterocyclylalkynes and their use as allosteric modulators of mGluR5 receptor activity, pharmaceutical compositions comprising such compounds, and methods of treatment therewith. Compounds of the invention can be used for the treatment and/or prevention of neurological and psychiatric disorders associated with glutamate dysfunction such as schizophrenia or cognitive decline, dementia or cognitive impairment, or other pathologies that can be related either directly or indirectly to glutamate dysfunction.

BACKGROUND TO THE INVENTION

Glutamate is the primary excitatory amino acid in the mammalian central nervous system. Neurotransmission mediated by glutamate has been demonstrated to be critical in many physiological processes, such as synaptic plasticity, long term potentiation involved in both learning and memory as well as sensory perception (Riedel et al., *Behav. Brain Res.* (2003), Vol. 140, pp. 1-47, in review). Furthermore, it has been demonstrated that an imbalance of glutamate neurotransmission plays a critical role in the pathophysiology of various neurological and psychiatric diseases.

The excitatory neurotransmission of glutamate is mediated through at least two different classes of receptors: ionotropic glutamate receptors such as the N-methyl-D-aspartate receptor (NMDA), α-amino-3-hydroxy-5-methyl-4-isoxazolepropionic acid receptor (AMPA) or kainate; and the metabotropic glutamate receptors (mGluR). The ionotropic receptors are ligand gated ion channels and are thought to be responsible for regulating the rapid neuronal transmission between two neurons. The metabotropic glutamate receptors are G-protein coupled receptors (GPCRs) which appear to mediate not only synaptic transmission, but also to regulate the extent of neurotransmitter release as well as post synaptic receptor activation.

Dysregulation in glutamatergic neurotransmission, for example through altered glutamate release or post-synaptic receptor activation, has been demonstrated in a variety of neurological as well as psychiatric disorders. Hypofunction of the NMDA receptor has not only been demonstrated in Alzheimer's patients, but is increasingly accepted as the putative cause of schizophrenia (Farber et al., *Prog. Brain Res.*, (1998), Vol. 116, pp. 421-437, Coyle et al., *Cell. and Mol. Neurobiol.*, (2006), Vol. 26, pp. 365-384). This is supported by clinical studies showing that antagonists of the NMDA receptor induce symptoms indistinguishable to those suffered by schizophrenia patients (Javitt et al., *Am J. Psychiatry*, (1991), Vol. 148, pp. 1301-1308; Meltzer HY, *Biol. Psychiatry*, (1999), Vol. 46(10), pp. 1321-1327). Therefore, approaches that could potentiate or normalize NMDA receptor signaling have the potential to treat neurological and psychiatric disorders. mGluR5, a G protein-coupled receptor that is encoded by the GRM5 gene, belongs to a superfamily of currently eight identified Type III GPCRs, which are unique in that the glutamate ligand binds to a large extracellular amino-terminal protein domain.

This superfamily is further divided into three groups (Groups I, II and III) based on amino acid homology as well as the intracellular signaling cascades they regulate (Schoepp et al., *Neuropharma*, (1999), Vol. 38, pp. 1431-1476) and pharmacological profile. mGluR5 belongs to Group I and is coupled to the phospholipase C signaling cascade which regulates intracellular calcium mobilization.

In the central nervous system (CNS), mGluR5 has been demonstrated to be expressed mainly in the cortex, hippocampus, nucleus accumbens and the caudate-putamen. These brain regions are known to be involved in memory formation and cognitive function as well as emotional response. mGluR5 has been shown to be localized post-synaptically, adjacent to the post-synaptic density (Lujan et al., *Eur. J. Neurosci.* (1996), Vol. 8, pp. 1488-1500). A functional interaction between mGluR5 and the NMDA receptor has also been demonstrated, where activation of mGluR5 potentiates the activation state of the NMDA receptor (Mannaioni et al., *NeuroSci.*, (2001), Vol. 21, pp. 5925-5924, Rosenbrock et al., *Eur. J. Pharma.*, (2010), Vol. 639, pp. 40-46). Furthermore, activation of mGluR5 has been demonstrated in pre-clinical, in vivo models to rescue cognitive impairment as well as psychotic disturbance induced by NMDA receptor antagonists (Chan et al., *Psychopharma.* (2008), Vol. 198, pp. 141-148). Therefore, activation of mGluR5, and thereby potentiation or normalization of the NMDA receptor signaling, is a potential mechanism for the treatment of psychiatric and neurological disorders.

Most agonists of mGluR5 bind the orthosteric glutamate binding site. Since the glutamate binding site between the mGluR family members is highly conserved, it has been challenging to develop selective mGluR5 agonists, which have acceptable CNS penetration and demonstrate in vivo activity.

An alternative approach to achieve selectivity between the mGluR family members is to develop compounds, which bind to an allosteric site, which is not as highly conserved between the family members. These allosteric binding compounds would not interfere with the natural glutamate binding and signaling, but modulate the receptor activation state. Allosteric ligands that have agonistic or inverse agonistic activity in the absence of orthosteric ligands are termed allosteric agonists or antagonists, respectively. Allosteric ligands lacking effect in the absence of orthosteric ligands are termed modulators (negative or positive).

Positive allosteric modulators of mGluR5 have recently been identified (O'Brien et al., *Mol. Pharma.* (2003), Vol. 64, pp. 731-740, Lindsley et al., *J. Med. Chem.* (2004), Vol. 47, pp. 5825-5828), where it has been determined that these compounds potentiate mGluR5 activity in the presence of bound glutamate. In the absence of bound glutamate, the mGluR5 positive modulators do not demonstrate any intrinsic activity.

Therefore, these compounds potentiate the natural signaling of mGluR5 as opposed to agonists, which activate the receptor in a permanent, unnatural manner. mGluR5 positive allosteric modulators therefore represent an approach to potentiate mGluR5 signaling which in turn potentiates and normalizes the NMDA receptor hypofunction detected in neurological and psychiatric disorders. mGluR5 negative allosteric modulators are useful to depress the mGluR5 signaling which in turn decreases and normalizes the NMDA receptor hyperfunction detected in some neurological, psychiatric disorders and in more general CNS disorders. Both types of allosteric modulator can also be related to some rare disease e.g. without any kind of limitation, Fragile-X syndrome, Rett syndrome, Phelan-McDermid syndrome or tuberous sclerosis.

SUMMARY OF THE INVENTION

The invention provides a compound having the general formula I:

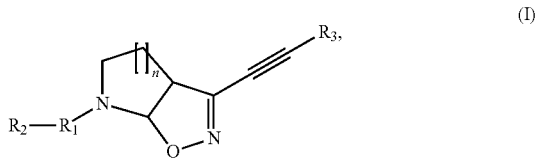

or an enantiomer, diastereomer, N-oxide, or a pharmaceutically acceptable salt thereof, wherein: $R_1$ is an alkyl group, an optionally substituted mono-, bi- or tricyclic $C_1$-$C_{13}$ heterocyclic group containing from 1 to 5 heteroatoms selected from N, O, and S, an optionally substituted mono-, bi- or tricyclic $C_6$-$C_{14}$ aryl group, an optionally substituted $C_3$-$C_6$ cycloalkyl group, an optionally substituted $C_3$-$C_6$ cycloalkenyl group, a bond, or an optionally substituted CO, CS, CH, $CH_2$ or $SO_2$ group;
$R_2$ is absent, or is an optionally substituted mono- or bicyclic $C_1$-$C_9$ heterocyclic group containing from 1 to 3 heteroatoms selected from N, O, and S, an optionally substituted mono-, bi- or tricyclic $C_6$-$C_{14}$ aryl group, or an optionally substituted group selected from alkyl, cycloalkyl, alkoxy, cycloalkyloxy, aryloxy, cycloalkyl, cycloalkyloxy, heteroaryloxy, alkylthio, amino, N-alkylamino, N,N-dialkylamino, N-alkyl-N-alkoxyamino or N-alkyl-Nalkyloxyamino; $R_3$ is an optionally substituted alkyl group, an optionally substituted mono-, bi- or tricyclic $C_1$-$C_{13}$ heterocyclic group containing from 1 to 5 heteroatoms selected from N, O, and S, an optionally substituted mono-, bi- or tricyclic $C_6$-$C_{14}$ aryl group, an optionally substituted $C_3$-$C_6$ cycloalkyl group, or an optionally substituted $C_3$-$C_6$ cycloalkenyl group; and
n is 1-3.

The optional substituents are independently selected from halogen atoms and $C_1$-$C_6$ alkyl, $C_1$-$C_6$ alkoxy, hydroxy, mercapto, nitro, cyano, oxo, halo($C_1$-$C_6$)alkyl, halo($C_1$-$C_6$) alkoxy, $C_1$-$C_6$ alkylthio, $C_1$-$C_6$ alkylsulphonyl, $C_1$-$C_6$ alkylcarbonyl, sulphamoyl, $C_1$-$C_6$ alkylsulphamoyl, di($C_1$-$C_6$) alkylsulphamoyl, ($C_1$-$C_6$)alkoxycarbonyl and ($C_1$-$C_6$) alkylcarbonyl($C_1$-$C_6$)alkyl groups, and from groups of the formulae —NR*R*, —C(=O)—NR*R*, -A, —O-A, —C(=O)-A, —(CH$_2$)q-A, —NR-A, —C(=O)—NR-A, —NR**C(=O)-A and —O—C(=O)-A wherein each R* independently represents a hydrogen atom or a $C_1$-$C_6$ alkyl, $C_1$-$C_6$ alkoxy, $C_1$-$C_6$ alkylcarbonyl, phenyl or benzyl group, R** represents a hydrogen atom or a $C_1$-$C_6$ alkyl group, q is an integer from 1 to 6 and A represents a phenyl group or a $C_1$-$C_8$ heterocyclic group containing from 1 to 3 heteroatoms selected from N, O and S; a $C_1$-$C_6$ cycloalkyl group; each group A being optionally substituted with from 1 to 3 groups independently selected from halo, hydroxy, cyano, nitro and $C_1$-$C_6$ alkyl, preferably wherein the optional substituents are selected from the groups consisting of halogen atoms and $C_1$-$C_6$ alkyl groups.

The most preferred compounds according to the invention are those in which $R_1$ represents a CO group and n is 1.

In an embodiment of the invention, $R_2$ preferably is an optionally substituted mono- or bicyclic $C_1$-$C_9$ heterocyclic group containing from 1 to 3 heteroatoms selected from nitrogen, oxygen and sulfur, or an optionally substituted group chosen from cycloalkyl, alkoxy, cycloalkyloxy, aryloxy, heteroaryloxy, amino, N-alkylamino, N,N-dialkylamino, or N-alkyl-N-alkoxyamino.

For example, when $R_2$ represents an optionally substituted mono- or bicyclic $C_1$-$C_9$ heterocyclic group containing from 1 to 3 heteroatoms selected from nitrogen, oxygen and sulfur, $R_2$ is preferably a 2-furyl, 5-methyl-2-furyl, 3-furyl, 4-morpholinyl, 4-oxanyl, piperidinyl, 1-methyl-4-piperidinyl, 4-methylpiperazinyl, 3-(1,5-dimethyl)pyrazolyl, 3-pyridylamino, pyrrolidinyl or 4-thiazolyl group.

For example, when $R_2$ represents an optionally substituted cycloalkyl group, $R_2$ is preferably a cyclopentyl or 4-(1,1-difluorocyclohexyl) group.

For example, when $R_2$ represents an optionally substituted alkoxy group, $R_2$ is preferably an ethoxy, isopropoxy, 2,2-dimethylpropoxy, t-butoxy or 3-methylbutoxy group.

For example, when $R_2$ represents an optionally substituted cycloalkyloxy group, $R_2$ is preferably a cyclopropylmethoxy or cyclopentoxy group.

For example, when $R_2$ represents an optionally substituted heteroaryloxy group, $R_2$ is preferably a 4-oxanyloxy group.

For example, when $R_2$ represents an optionally substituted amino group, $R_2$ is preferably an isopropylamino, 2,2-dimethylpropylamino, t-butylamino, 3-pentylamino cyclopentylamino or a 3-pyridylamino group.

For example, when $R_2$ represents an optionally substituted N-alkylamino, N,N-dialkylamino, or N-alkyl-N-alkoxyamino group, $R_2$ is preferably an N,N-dimethyl, N,N-diethyl, N-ethyl-N-isopropyl, N-methoxy-N-methyl or N-(2-methoxyethyl)-N-methyl group.

In an alternative embodiment of the invention, $R_2$ preferably represents a group having the formula:

wherein $R_4$ is a $C_1$-$C_{10}$ linear or branched alkyl group, a $C_1$-$C_{10}$ cycloalkyl group or a $C_1$-$C_{10}$ heterocyclic group containing at least one heteroatom selected from N or O.

For example, when $R_4$ is a $C_1$-$C_{10}$ linear or branched alkyl group, $R_4$ is preferably an ethyl, isopropyl, 2,2-dimethylpropyl, t-butyl or 3-methylbutyl group so that $R_2$ is preferably an ethoxy, isopropoxy, 2,2-dimethylpropoxy, t-butoxy or 3-methylbutoxy group.

For example, when $R_4$ is a $C_1$-$C_{10}$ a cycloalkyl group, $R_4$ is preferably a cyclopropylmethyl or a cyclopentyl group so that $R_2$ is preferably a cyclopropylmethoxy or cyclopentoxy group.

For example, when $R_4$ is a $C_1$-$C_{10}$ heterocyclic group containing at least one heteroatom selected from N or O, $R_4$ is preferably a 4-oxanyl group so that $R_2$ is a 4-oxanyloxy group.

In an alternative embodiment of the invention, $R_2$ preferably is a saturated or unsaturated, optionally substituted, five or six membered homocyclic group or heterocyclic group containing at least one heteroatom selected from N or O.

For example, when $R_2$ is an optionally substituted, five membered homocyclic group, $R_2$ is preferably a cyclopentyl group. When $R_2$ an optionally substituted six membered homocyclic group, $R_2$ is preferably a 4-(1,1-difluorocyclohexyl) group.

For example, when $R_2$ is an optionally substituted, five membered heterocyclic group containing at least one heteroatom selected from N or O, $R_2$ is preferably a 2-furyl, 5-methyl-2-furyl, 3-furyl, 3-(1,5-dimethyl)pyrazolyl, pyrrolidinyl or 4-thiazolyl group. When $R_2$ is an optionally substituted, five membered heterocyclic group containing at least one heteroatom selected from N or O, $R_2$ is preferably a 4-morpholinyl, 4-oxanyl, piperidinyl, 1-methyl-4-piperidinyl, 4-methylpiperazinyl or 3-pyridylamino group.

In an alternative embodiment of the invention, $R_2$ preferably represents a group having the formula:

—$NR_5R_6$ wherein $R_5$ is a $C_1$-$C_{10}$ linear or branched alkyl or alkoxy group or hydrogen; $R_6$ is a $C_1$-$C_{10}$ linear or branched alkyl or alkoxy group, $R_5$ and $R_6$ being the same or different; or wherein $R_5$ and $R_6$ together with the nitrogen atom form a five or six membered heterocyclic ring.

For example, when $R_5$ or $R_6$ is a $C_1$-$C_{10}$ linear or branched alkyl group, $R_5$ or $R_6$ is preferably a methyl, ethyl, isopropyl, 2,2-dimethylpropyl, t-butyl or 3-pentyl group and $R_2$ is preferably an N,N-dimethyl, N,N-diethyl, N-ethyl-N-isopropyl, isopropylamino, t-butylamino, 3-pentylamino or 2,2-dimethylpropylamino group.

For example, when $R_5$ or $R_6$ is a $C_1$-$C_{10}$ linear or branched alkoxy group, $R_5$ or $R_6$ is preferably a methoxy or 2-methoxyethyl group and $R_2$ is preferably an N-methoxy-N-methyl or N-(2-methoxyethyl)-N-methyl group.

For example, when $R_5$ and $R_6$ together with the nitrogen atom form a five or six membered heterocyclic ring, $R_2$ is preferably a 4-methylpiperazinyl, 4-morpholinyl, piperidinyl or pyrrolidinyl group.

In an embodiment of the invention, $R_3$ preferably is an optionally substituted mono-, bi- or tricyclic $C_6$-$C_{14}$ aryl group, an optionally substituted, five or six membered heterocyclic group containing at least one heteroatom selected from N or O, an optionally substituted $C_3$-$C_6$ cycloalkyl group, or an optionally substituted $C_3$-$C_6$ cycloalkenyl group. For example, when $R_3$ is an optionally substituted mono-, bi- or tricyclic $C_6$-$C_{14}$ aryl group, $R_3$ is preferably a phenyl group. When $R_3$ is an optionally substituted, five or six membered heterocyclic group containing at least one heteroatom selected from N or O, $R_3$ is preferably a pyridyl group.

In an alternative embodiment of the invention, $R_3$ is most preferably an optionally substituted phenyl or pyridyl group, with said optional substituents being selected from a $C_1$-$C_{10}$ alkyl group or a halide group. For example, $R_3$ represents a phenyl, 3-methylphenyl, 3-bromophenyl, 3-chlorophenyl, 3-fluorophenyl or 6-methyl-2-pyridyl group.

In an alternative embodiment of the invention, $R_1$ represents an optionally substituted CO group, $R_2$ is absent, $R_3$ represents a phenyl, 3-bromophenyl, 3-chlorophenyl, 3-fluorophenyl, 3-methylphenyl or a 6-methyl-2-pyridyl group and n is 1.

In an embodiment of the invention, a compound, or an enantiomer, diastereomer, N-oxide, or a pharmaceutically acceptable salt, is provided according to general formula I selected from:

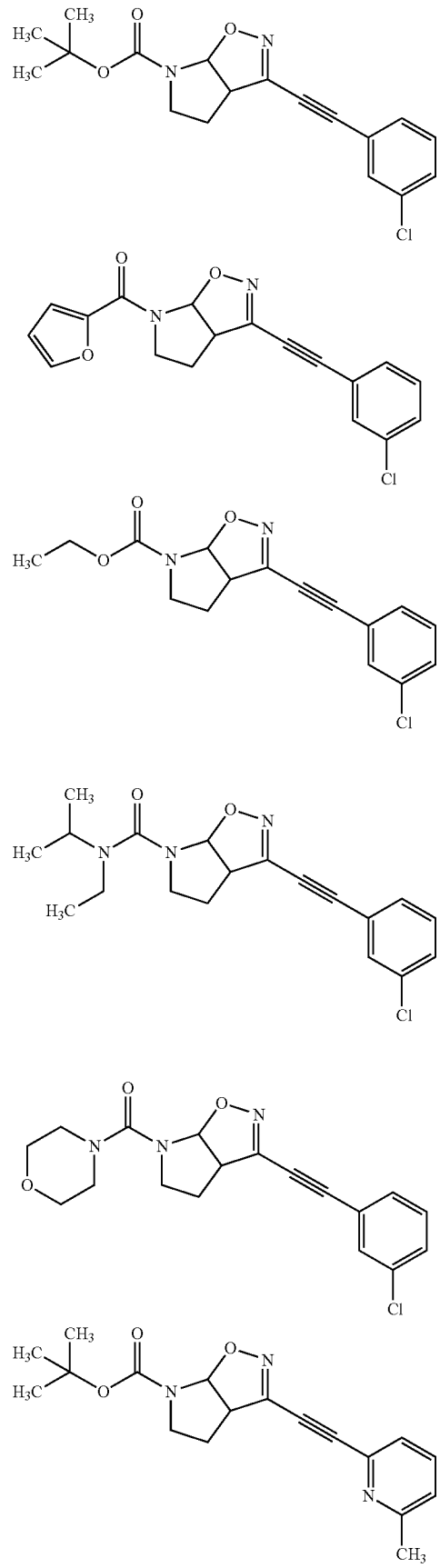

-continued
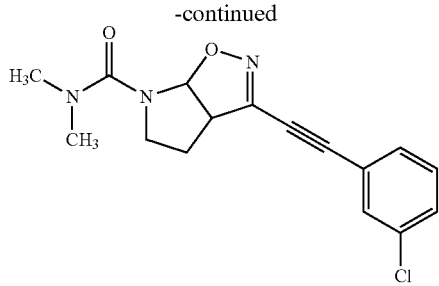
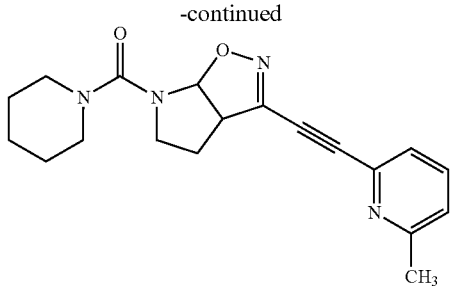
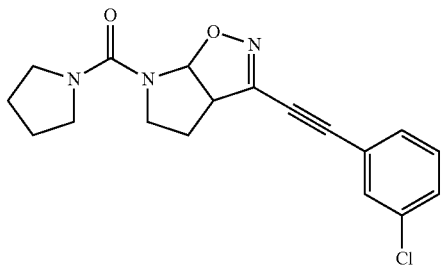
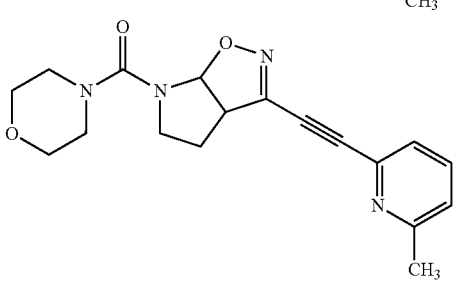
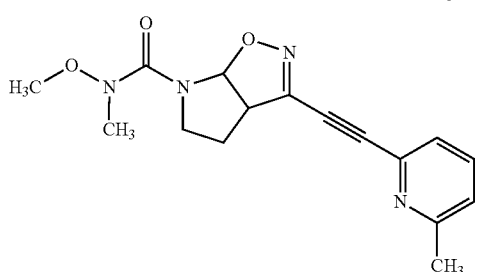
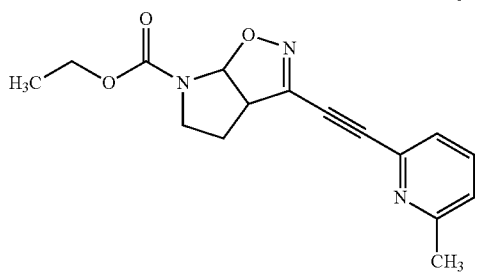
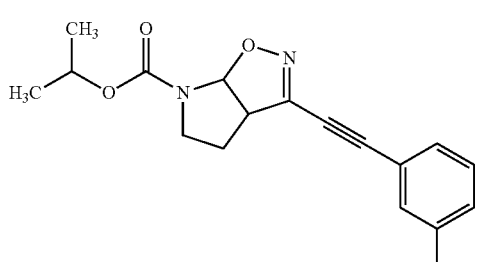
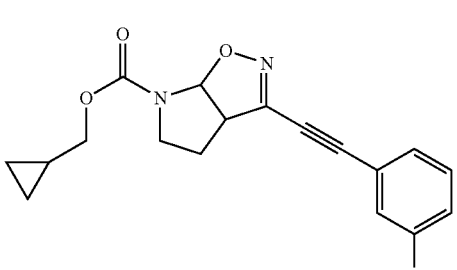

-continued
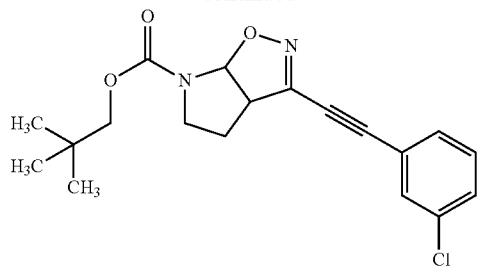
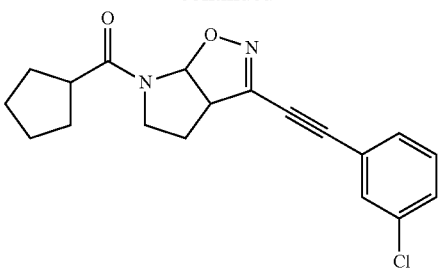
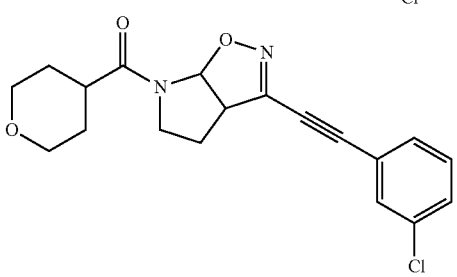
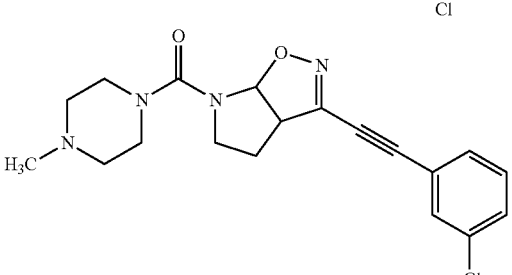
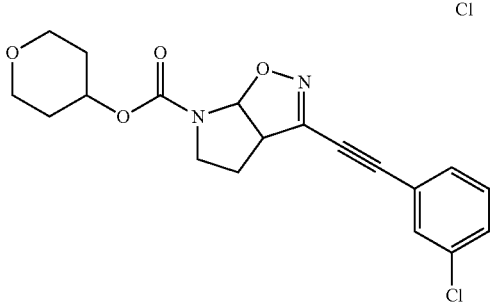
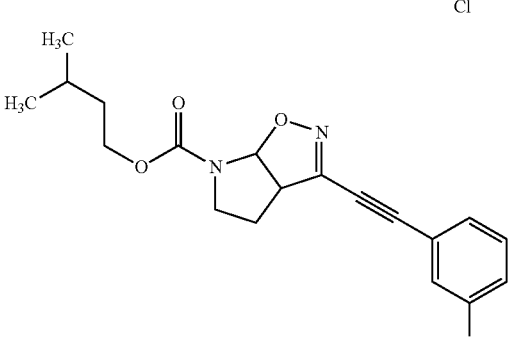
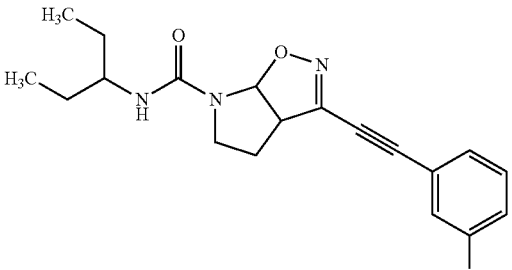

-continued

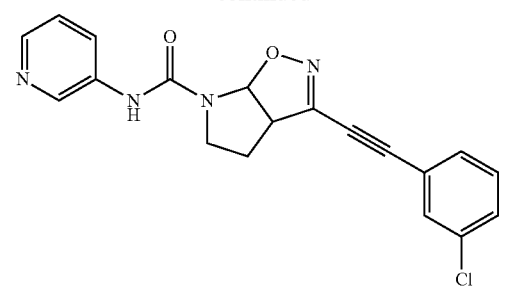
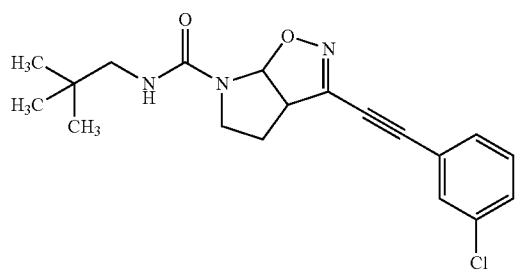
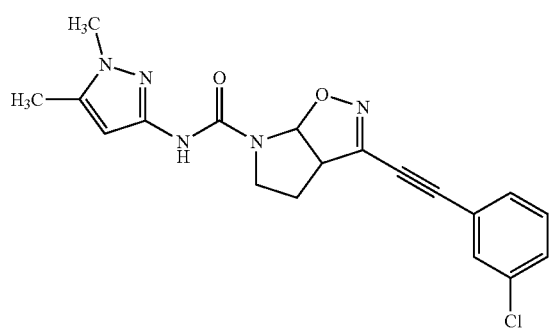
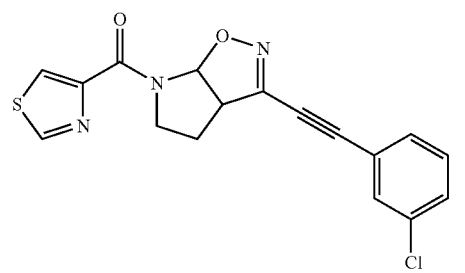
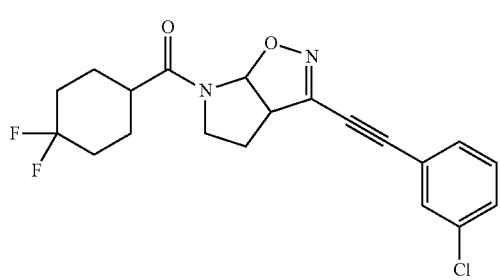
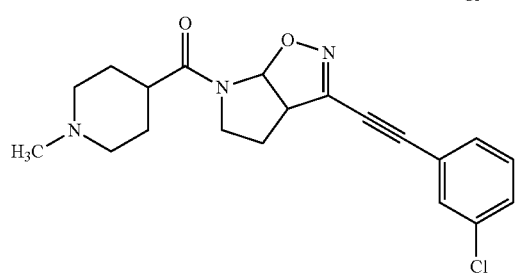

-continued

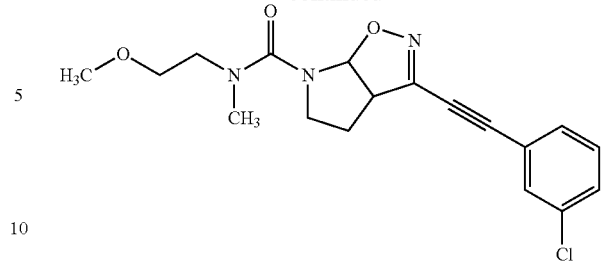
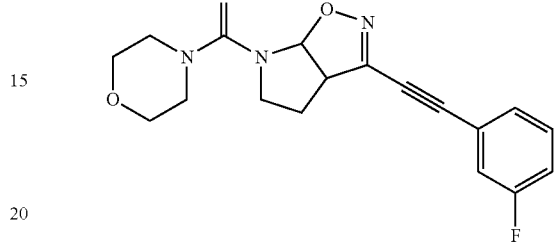
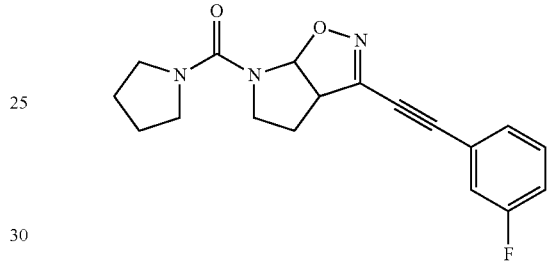
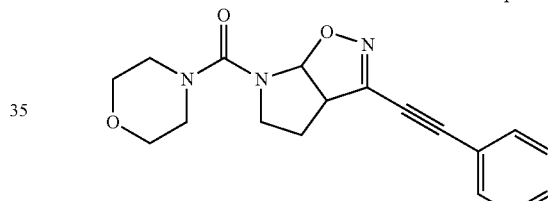
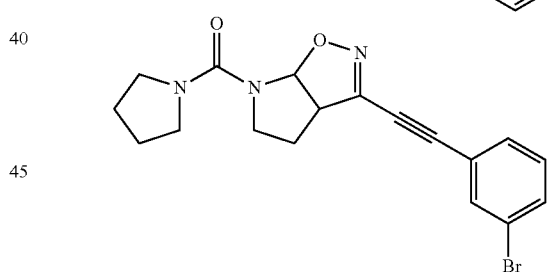
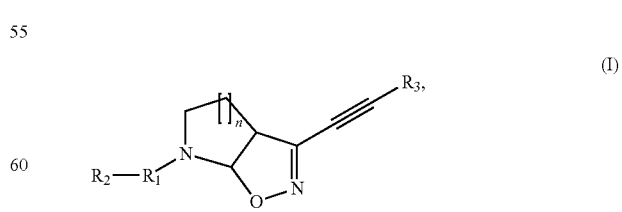

In a further embodiment of the invention, a pharmaceutical composition is preferably provided comprising a compound of Formula I, $$\text{(I)}$$

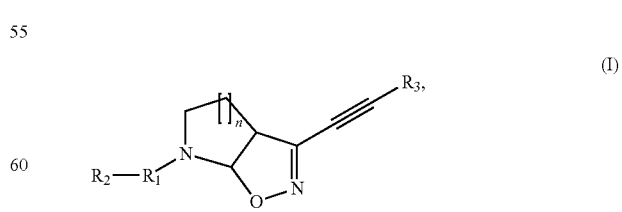

or an enantiomer, diastereomer, N-oxide, or a pharmaceutically acceptable salt thereof, and a pharmaceutically acceptable carrier, wherein $R_1$ is an alkyl group, an optionally substituted mono-, bi- or tricyclic $C_1$-$C_{13}$ heterocyclic group containing 1 to 5 heteroatoms selected from N, O, and S; an optionally substituted mono-, bi- or tricyclic $C_6$-$C_{14}$ aryl group, an optionally substituted $C_3$-$C_6$ cycloalkyl group, or an optionally substituted $C_3$-$C_6$ cycloalkenyl group; or a bond, CO, CS, CH, $CH_2$, $SO_2$ group optionally substituted by one or more $R_2$ group or substituent; $R_2$ is absent or is an optionally substituted mono- or bicyclic $C_1$-$C_9$ heterocyclic group containing from 1 to 3 heteroatoms selected from nitrogen, oxygen and sulfur, an optionally substituted mono-, bi- or tricyclic $C_6$-$C_{14}$ aryl group, or an optionally substituted group chosen from alkyl, cycloalkyl, alkoxy, cycloalkyloxy, aryloxy, heteroaryloxy, alkylthio, amino, N-alkylamino, N,N-dialkylamino or N-alkyl-N-alkoxyamino; $R_3$ is an optionally substituted alkyl group, an optionally substituted mono-, bi- or tricyclic $C_1$-$C_{13}$ heterocyclic group containing 1 to 5 heteroatoms selected from N, O, and S; an optionally substituted mono-, bi- or tricyclic $C_6$-$C_{14}$ aryl group, an optionally substituted $C_3$-$C_6$ cycloalkyl group, or an optionally substituted $C_3$-$C_6$ cycloalkenyl group; and
n is 1-3.

In another embodiment of the invention, a compound of Formula I,

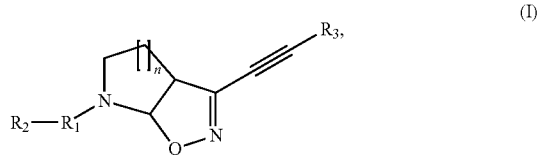

(I)

or an enantiomer, diastereomer, N-oxide, or a pharmaceutically acceptable salt thereof, for use in the treatment and/or prevention of a neurological disorder, psychotic disorder, or a psychiatric disorder associated with glutamate dysfunction is preferably provided, wherein $R_1$ is an alkyl group, an optionally substituted mono-, bi- or tricyclic $C_1$-$C_{13}$ heterocyclic group containing 1 to 5 heteroatoms selected from N, O, and S; an optionally substituted mono-, bi- or tricyclic $C_6$-$C_{14}$ aryl group, an optionally substituted $C_3$-$C_6$ cycloalkyl group, or an optionally substituted $C_3$-$C_6$ cycloalkenyl group; or a bond, CO, CS, CH, $CH_2$, $SO_2$ group optionally substituted by one or more $R_2$ group or substituent; $R_2$ is absent or is an optionally substituted mono- or bicyclic $C_1$-$C_9$ heterocyclic group containing from 1 to 3 heteroatoms selected from nitrogen, oxygen and sulfur, an optionally substituted mono-, bi- or tricyclic $C_6$-$C_{14}$ aryl group, or an optionally substituted group chosen from alkyl, cycloalkyl, alkoxy, cycloalkyloxy, aryloxy, heteroaryloxy, alkylthio, amino, N-alkylamino, N,N-dialkylamino or N-alkyl-N-alkoxyamino; $R_3$ is an optionally substituted alkyl group, an optionally substituted mono-, bi- or tricyclic $C_1$-$C_{13}$ heterocyclic group containing 1 to 5 heteroatoms selected from N, O, and S; an optionally substituted mono-, bi- or tricyclic $C_6$-$C_{14}$ aryl group, an optionally substituted $C_3$-$C_6$ cycloalkyl group, or an optionally substituted $C_3$-$C_6$ cycloalkenyl group; and n is 1-3.

In an embodiment of the invention, a compound according to Formula I is used in the treatment and/or prevention of a neurological disorder, psychotic disorder, or a psychiatric disorder associated with glutamate dysfunction.

Preferably the neurological disorder, psychotic disorder, or psychiatric disorder associated with glutamate dysfunction is schizophrenia, schizoaffective disorder, substance induced psychotic disorder, age-associated learning and memory impairments or losses, post stroke dementia, deficits in concentration, mild cognitive impairment, cognitive dysfunction in Alzheimers disease, cognitive dysfunction of schizophrenia, cognitive decline, dementia or cognitive impairment.

More preferably the disorder is Fragile-X syndrome, Rett syndrome, Phelan-McDermid syndrome, or tuberous sclerosis.

TERMS AND DEFINITIONS USED

Except where stated otherwise, the following definitions apply throughout the present specification and claims. These definitions apply regardless of whether a term is used by itself or in combination with other terms. For example, the definition of "alkyl" applies not only to alkyl groups per se, but also to the alkyl portions of alkoxy, alkylamino, alkylthio or alkylcarbonyl groups etc. Furthermore all ranges described for a chemical group, for example "from 1 to 13 carbon atoms" or "$C_1$-$C_6$ alkyl" include all combinations and sub-combinations of ranges and specific numbers of carbon atoms therein.

"Alkyl" means a straight chain or branched chain aliphatic hydrocarbon group having from 1 to 20 carbon atoms in the chain. Preferred alkyl groups have from 1 to 12 carbon atoms in the chain. More preferred alkyl groups have from 1 to 6 carbon atoms in the chain. "Lower alkyl" means an alkyl group having about 1 to about 6 carbon atoms in the chain which may be straight or branched. Examples of suitable alkyl groups include methyl, ethyl, n-propyl, isopropyl, sec-butyl, n-butyl, and t-butyl.

"Alkenyl" means a straight chain or branched chain aliphatic hydrocarbon group having at least one carbon-carbon double bond and having from 2 to 15 carbon atoms in the chain. Preferred alkenyl groups have from 2 to 12 carbon atoms in the chain. More preferred alkenyl groups have from 2 to 6 carbon atoms in the chain. "Lower alkenyl" means an alkenyl group having 2 to about 6 carbon atoms in the chain, which may be straight or branched. Examples of suitable alkenyl groups include ethenyl, propenyl, isopropenyl, n-butenyl, 1-hexenyl and 3-methylbut-2-enyl.

"Alkynyl" means a straight chain or branched chain aliphatic hydrocarbon group having at least one carbon-carbon triple bond and having from 2 to 15 carbon atoms in the chain. Preferred alkynyl groups have from 2 to 12 carbon atoms in the chain. More preferred alkynyl groups have from 2 to 6 carbon atoms in the chain. "Lower alkynyl" means an alkynyl group having 2 to about 6 carbon atoms in the chain, which may be straight or branched. Examples of suitable alkynyl groups include ethynyl, propynyl and 2-butynyl.

"Mono-, bi-, or tricyclic heterocyclic" means an aromatic or non-aromatic saturated mono- bi- or tricyclic ring system having from 2 to 14 ring carbon atoms, and containing from 1 to 5 ring atoms selected from N, O and S, alone or in combination. Bi- and tricyclic heterocyclic groups are fused at 2 or 4 points or joined at one point via a bond or a heteroatom linker (O, S, NH, or N($C_1$-$C_6$ alkyl). The "mono- bi- or tricyclic heterocyclic" can be optionally substituted on the ring by replacing an available hydrogen on the ring by one or more substituents which may be the same or different. The nitrogen or sulphur atom of the heterocyclic can be optionally oxidized to the corresponding N-oxide, S-oxide or S-dioxide. Examples of suitable heterocyclics include furanyl, imidazolyl, isoxazolyl, oxadiazolyl, oxazolyl, pyrrolyl, pyridyl, pyrimidyl, pyridazinyl, thiazolyl, triazolyl, tetrazolyl, thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl and benzoisoxazolyl, aziridinyl, piperidinyl, pyrrolidinyl, piperazinyl, tetrahydropyranyl, tetrahydrofuranyl, tetrahydrothiophenyl, morpholinyl and thiomorpholinyl.

Heterocyclics with aromatic characteristics may be referred to as heteroaryls or heteroaromatics. Examples of suitable heteroaromatics include furanyl, imidazolyl, isoxazolyl, oxadiazolyl, oxazolyl, pyrrolyl, pyridyl, pyrimidyl, pyridazinyl, thiazolyl, triazolyl, tetrazolyl, thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisoxazolyl, tetrahydroquinolinyl, tetrahydroisoquinolinyl, 3-phenylpyridine, 3-cyclohexylpyridine, 3-(pyridin-3-yl) morpholine, 3-phenylisoxazole and 2-(piperidin-1-yl)pyrimidine.

"Mono-, bi- or tricyclic aryl" means an aromatic monocyclic, bicyclic or tricyclic ring system comprising 6 to 14 carbon atoms. Bi- and tricyclic aryl groups are fused at 2 or 4 points or joined at one point via a bond or a heteroatom linker (O, S, NH, or $N(C_1-C_6$ alkyl) (e.g., biphenyl, 1-phenylnapthyl). The aryl group can be optionally substituted on the ring with one or more substituents, preferably 1 to 6 substituents, which may be the same or different. Examples of suitable aryl groups include phenyl and naphthyl.

"Cycloalkyl" means a monocyclic or bicyclic carbon ring system having from 3 to 14 carbon atoms, preferably from 3 to 6 carbon atoms. The cycloalkyl can be optionally substituted on the ring by replacing an available hydrogen on the ring by one or more substituents which may be the same or different. Examples of suitable monocyclic cycloalkyls include cyclopropyl, cyclopentyl, cyclohexyl and cycloheptyl. Examples of suitable multicyclic cycloalkyls include 1-decalinyl, norbornyl and adamantyl.

"Cycloalkenyl" has a meaning corresponding to that of cycloalkyl, but with one or two double bonds within the ring (e.g., cyclohexenyl, cyclohexadiene).

"Amines" are derivatives of ammonia, wherein one or more hydrogen atoms have been replaced by a substituent such as an alkyl or aryl group. These may respectively be called alkylamines and arylamines; amines in which both types of substituent are attached to one nitrogen atom may be called alkylarylamines.

Amines can be further organized into four sub-categories. Primary amines arise when one of the three hydrogen atoms in ammonia is replaced by an alkyl or aromatic group (an N-alkylamino or N-arylamino respectively). Examples of suitable primary alkyl amines include methylamine or ethanolamine, or aniline (phenylamine) as an example of an aromatic amine. Secondary amines have two organic substituents (independently alkyl or aryl groups) bound to the nitrogen atom together with one hydrogen (or no hydrogen if one of the substituent bonds is double). Examples of suitable secondary amines include dimethylamine and methylethanolamine, while an example of an aromatic amine would be diphenylamine. Such compounds may also be referred to as "N,N-dialkylamino", "N,N-diarylamino" or "N,N-alkylarylamino" groups depending on the nature of the substituents. A secondary amine substituted by an alkoxy group, as defined herein, would be termed an "N-alkyl-N-alkoxyamino" compound for example. In tertiary amines, all three hydrogen atoms are replaced by organic substituents, such as trimethylamine. The final sub-category is cyclic amines which are either secondary or tertiary amines. Examples of suitable cyclic amines include the 3-member ring aziridine and the six-membered ring piperidine. N-methylpiperidine and N-phenylpiperidine are suitable examples of cyclic tertiary amines.

"Amides" are compounds with a nitrogen atom attached to a carbonyl group, thus having the structure R—CO—NR'R", with groups R' and R" being independently selected from alkyl or aromatic groups as defined herein. For example when R' is hydrogen and R" is a 3-pyridyl group, the resulting amide has a 3-pyridylamino substituent. Alternatively when R' is hydrogen and R" is a cyclopentyl group, the resulting amide has a cyclopentylamino substituent.

"Halogen" or "Hal" means fluorine, chlorine, bromine or iodine. Preferred halogens are fluorine, chlorine or bromine, and most preferred are fluorine and chlorine.

The term "acyl", whether used alone, or within a term such as "acylamino", denotes a radical provided by the residue after removal of hydroxyl from an organic acid. The term "acylamino" refers an amino radical substituted with an acyl group. An example of an "acylamino" radical is $CH_3C(=O)$—NH— where the amine may be further substituted with alkyl, aryl or aralkyl.

An asterisk may be used in sub-formulas to indicate the bond, which is connected to a parent or core molecule as defined herein.

Stereochemistry

Unless specifically indicated, throughout the specification and claims, a given chemical formula or name shall encompass tautomers and all stereo, optical and geometrical isomers (e.g. enantiomers, diastereomers, E/Z isomers etc.) and racemates thereof. This includes mixtures in different proportions of the separate enantiomers, mixtures of diastereomers, or mixtures of any of the foregoing forms where such isomers and enantiomers exist, as well as salts, including pharmaceutically acceptable salts and solvates thereof such as hydrates, solvates of the free compounds or solvates of a salt of the compound.

Derivatives of Compounds of the Invention

The invention further encompasses salts, solvates, hydrates, N-oxides, produgs and active metabolites of the compounds of formula I.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamidobenzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals such as aluminium, calcium, lithium, magnesium, potassium, sodium, zinc and the like (see Pharmaceutical salts, Berge, S. M. et al., *J. Pharm. Sci.*, (1977), Vol. 66, pp. 1-19).

Pharmaceutically acceptable salts of the present invention can be synthesized from the parent compound, which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts), also comprise a part of the invention.

Typically, a pharmaceutically acceptable salt of a compound of formula I may be readily prepared by using a desired acid or base as appropriate. The salt may precipitate from solution and be collected by filtration or may be recovered by evaporation of the solvent. For example, an aqueous solution of an acid such as hydrochloric acid may be added to an aqueous suspension of a compound of formula I and the resulting mixture evaporated to dryness (lyophilized) to obtain the acid addition salt as a solid. Alternatively, a compound of formula I may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

The acid addition salts of the compounds of formula I may be prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the invention.

Also included are both total and partial salts, that is to say salts with 1, 2 or 3, preferably 2, equivalents of base per mole of acid of formula I or salts with 1, 2 or 3 equivalents, preferably 1 equivalent, of acid per mole of base of formula I.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine.

The base addition salts of said acidic compounds are prepared by contacting the free acid form with a sufficient amount of the desired base to produce the salt in the conventional manner. The free acid form may be regenerated by contacting the salt form with an acid and isolating the free acid.

Compounds of the invention may have both a basic and an acidic center and may therefore be in the form of zwitterions or internal salts.

Typically, a pharmaceutically acceptable salt of a compound of formula I may be readily prepared by using a desired acid or base as appropriate. The salt may precipitate from solution and be collected by filtration or may be recovered by evaporation of the solvent. For example, an aqueous solution of an acid such as hydrochloric acid may be added to an aqueous suspension of a compound of formula I and the resulting mixture evaporated to dryness (lyophilized) to obtain the acid addition salt as a solid. Alternatively, a compound of formula I may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The salts of the compound of formula I may form solvates (e.g., hydrates) and the invention also includes all such solvates. The meaning of the word "solvates" is well known to those skilled in the art as a compound formed by interaction of a solvent and a solute (i.e., solvation). Techniques for the preparation of solvates are well established in the art (see, for example, Brittain. *Polymorphism in Pharmaceutical Solids.* Marcel Decker, New York, 1999.).

The invention also encompasses N-oxides of the compounds of formulas I. The term "N-oxide" means that for heterocycles containing an otherwise unsubstituted $sp^2$ N atom, the N atom may bear a covalently bound O atom, i.e., —N→O. Examples of such N-oxide substituted heterocycles include pyridyl N-oxides, pyrimidyl N-oxides, pyrazinyl N-oxides and pyrazolyl N-oxides.

The invention also encompasses prodrugs of the compounds of formula I, i.e., compounds which release an active parent drug according to formula I in vivo when administered to a mammalian subject. A prodrug is a pharmacologically active or more typically an inactive compound that is converted into a pharmacologically active agent by a metabolic transformation. Prodrugs of a compound of formula I are prepared by modifying functional groups present in the compound of formula I in such a way that the modifications may be cleaved in vivo to release the parent compound. In vivo, a prodrug readily undergoes chemical changes under physiological conditions (e.g., are acted on by naturally occurring enzyme(s)) resulting in liberation of the pharmacologically active agent. Prodrugs include compounds of formula I wherein a hydroxy, amino, or carboxy group of a formula I compound is bonded to any group that may be cleaved in vivo to regenerate the free hydroxyl, amino or carboxy group, respectively. Examples of prodrugs include esters (e.g., acetate, formate, and benzoate derivatives) of compounds of formula I or any other derivative, which upon being brought to the physiological pH or through enzyme action is converted to the active parent drug. Conventional procedures for the selection and preparation of suitable prodrug derivatives are described in the art (see, for example, Bundgaard. *Design of Prodrugs*. Elsevier, 1985).

Prodrugs may be administered in the same manner as the active ingredient to which they convert or they may be delivered in a reservoir form, e.g., a transdermal patch or other reservoir which is adapted to permit (by provision of an enzyme or other appropriate reagent) conversion of a prodrug to the active ingredient slowly over time, and delivery of the active ingredient to the patient.

The invention also encompasses metabolites. A "metabolite" of a compound disclosed herein is a derivative of a compound which is formed when the compound is metabolised. The term "active metabolite" refers to a biologically active derivative of a compound, which is formed when the compound is metabolised. The term "metabolised" refers to the sum of the processes by which a particular substance is changed in the living body. In brief, all compounds present in the body are manipulated by enzymes within the body in order to derive energy and/or to remove them from the body. Specific enzymes produce specific structural alterations to the compound. For example, cytochrome P450 catalyses a variety of oxidative and reductive reactions while uridine diphosphate glucuronyltransferases catalyse the transfer of an activated glucuronic-acid molecule to aromatic alcohols, aliphatic alcohols, carboxylic acids, amines and free sulphydryl groups. Further information on metabolism may be obtained from *The Pharmacological Basis of Therapeutics*, 9th Edition, McGraw-Hill (1996), pages 11-17.

Metabolites of the compounds disclosed herein can be identified either by administration of compounds to a host and analysis of tissue samples from the host, or by incubation of compounds with hepatic cells in vitro and analysis of the resulting compounds. Both methods are well known in the art.

The term "carrier" refers to a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

The compounds of the invention may be formulated for administration in any convenient way for use in human or veterinary medicine and the invention therefore includes within its scope pharmaceutical compositions comprising a compound of the invention adapted for use in human or veterinary medicine. Such compositions may be presented for use in a conventional manner with the aid of one or more suitable carriers. Acceptable carriers for therapeutic use are well-known in the pharmaceutical art, and are described, for example, in Remington's Pharmaceutical Sciences, Mack Publishing Co. (A. R. Gennaro edit. 1985). The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s).

Pharmaceutical Compositions Comprising a Compound of Formula I

While it is possible that a compound I may be administered as the bulk substance, it is preferable to present the active ingredient in a pharmaceutical formulation, e.g., wherein the agent is in admixture with a pharmaceutically acceptable carrier selected with regard to the intended route of administration and standard pharmaceutical practice.

Accordingly, the invention further provides a pharmaceutical composition comprising a compound of formula I or a solvate, hydrate, enantiomer, diastereomer, N-oxide or pharmaceutically acceptable salt thereof in admixture with a pharmaceutically acceptable carrier. The term "carrier" refers to a diluent, excipient, and/or vehicle with which an active compound is administered.

A compound of formula I may be used in combination with other therapies and/or active agents. Accordingly, the invention provides, in a further aspect, a pharmaceutical composition comprising a compound of formula I or a solvate, hydrate, enantiomer, diastereomer, N-oxide or pharmaceutically acceptable salt thereof, a second active agent, and a pharmaceutically acceptable carrier.

The pharmaceutical compositions may comprise as, in addition to, the carrier any suitable binder, lubricant, suspending agent, coating agent and/or solubilizing agent.

Preservatives, stabilizers, dyes and flavouring agents also may be provided in the pharmaceutical composition. Antioxidants and suspending agents may be also used.

The compounds of the invention may be milled using known milling procedures such as wet milling to obtain a particle size appropriate for tablet formation and for other formulation types. Finely divided (nanoparticulate) preparations of the compounds of the invention may be prepared by processes known in the art, for example see WO02/00196.

Routes of Administration and Unit Dosage Forms

The routes for administration include oral (e.g., as a tablet, capsule, or as an ingestible solution), topical, mucosal (e.g., as a nasal spray or aerosol for inhalation), nasal, parenteral (e.g., by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual. The compositions of the invention may be especially formulated for any of those administration routes. In preferred embodiments, the pharmaceutical compositions of the invention are formulated in a form that is suitable for oral delivery.

There may be different composition/formulation requirements depending on the different delivery systems. It is to be understood that not all of the compounds need to be administered by the same route. Likewise, if the composition comprises more than one active component, then those components may be administered by different routes. By way of example, the pharmaceutical composition of the invention may be formulated to be delivered using a minipump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be delivered by multiple routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile. For example, the compound of Formula I may be coated with an enteric coating layer. The enteric coating layer material may be dispersed or dissolved in either water or in a suitable organic solvent. As enteric coating layer polymers, one or more, separately or in combination, of the following can be used; e.g., solutions or dispersions of methacrylic acid copolymers, cellulose acetate phthalate, cellulose acetate butyrate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating layer polymer(s). For environmental reasons, an aqueous coating process may be preferred. In such aqueous processes methacrylic acid copolymers are most preferred.

When appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For buccal or sublingual administration the compositions may be administered in the form of tablets or lozenges, which can be formulated in a conventional manner.

When the composition of the invention is to be administered parenterally, such administration includes one or more of: intravenously, intraarterially, intraperitoneally, intrathecally, intraventricularly, intraurethrally, intrasternally, intracranially, intramuscularly or subcutaneously administering the agent; and/or by using infusion techniques.

Pharmaceutical compositions of the invention can be administered parenterally, e.g., by infusion or injection. Pharmaceutical compositions suitable for injection or infusion may be in the form of a sterile aqueous solution, a dispersion or a sterile powder that contains the active ingredient, adjusted, if necessary, for preparation of such a sterile solution or dispersion suitable for infusion or injection. This preparation may optionally be encapsulated into liposomes. In all cases, the final preparation must be sterile, liquid, and stable under production and storage conditions. To improve storage stability, such preparations may also contain a preservative to prevent the growth of microorganisms. Prevention of the action of micro-organisms can be achieved by the addition of various antibacterial and antifungal agents, e.g., paraben, chlorobutanol, or acsorbic acid.

In many cases isotonic substances are recommended, e.g., sugars, buffers and sodium chloride to assure osmotic pressure similar to those of body fluids, particularly blood. Prolonged absorption of such injectable mixtures can be achieved by introduction of absorption-delaying agents, such as aluminium monostearate or gelatin.

Dispersions can be prepared in a liquid carrier or intermediate, such as glycerin, liquid polyethylene glycols, triacetin oils, and mixtures thereof. The liquid carrier or intermediate can be a solvent or liquid dispersive medium that contains, for example, water, ethanol, a polyol (e.g., glycerol, propylene glycol or the like), vegetable oils, non-toxic glycerine esters and suitable mixtures thereof. Suitable flowability may be maintained, by generation of liposomes, administration of a suitable particle size in the case of dispersions, or by the addition of surfactants.

For parenteral administration, the compound is best used in the form of a sterile aqueous solution, which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Sterile injectable solutions can be prepared by mixing a compound of formula I with an appropriate solvent and one or more of the aforementioned carriers, followed by sterile filtering. In the case of sterile powders suitable for use in the preparation of sterile injectable solutions, preferable preparation methods include drying in vacuum and lyophilization, which provide powdery mixtures of the aldosterone receptor antagonists and desired excipients for subsequent preparation of sterile solutions.

The compounds according to the invention may be formulated for use in human or veterinary medicine by injection (e.g., by intravenous bolus injection or infusion or via intramuscular, subcutaneous or intrathecal routes) and may be presented in unit dose form, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilizing, solubilizing and/or dispersing agents. Alternatively the active ingredient may be in sterile powder form for reconstitution with a suitable vehicle, e.g., sterile, pyrogen-free water, before use.

The compounds of the invention can be administered (e.g., orally or topically) in the form of tablets, capsules, ovules, elixirs, solutions or suspensions, which may contain flavouring or colouring agents, for immediate-, delayed-, modified-, sustained-, pulsed- or controlled-release applications.

The compounds of the invention may also be presented for human or veterinary use in a form suitable for oral or buccal administration, for example in the form of solutions, gels, syrups, mouth washes or suspensions, or a dry powder for constitution with water or other suitable vehicle before use, optionally with flavouring and colouring agents. Solid compositions such as tablets, capsules, lozenges, pastilles, pills, boluses, powder, pastes, granules, bullets or premix preparations may also be used. Solid and liquid compositions for oral use may be prepared according to methods well-known in the art. Such compositions may also contain one or more pharmaceutically acceptable carriers and excipients which may be in solid or liquid form.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia.

Additionally, lubricating agents such as magnesium stearate, stearic acid, glyceryl behenate and talc may be included.

The compositions may be administered orally, in the form of rapid or controlled release tablets, microparticles, mini tablets, capsules, sachets, and oral solutions or suspensions, or powders for the preparation thereof. In addition to the new solid-state forms of pantoprazole of the invention as the active substance, oral preparations may optionally include various standard pharmaceutical carriers and excipients, such as binders, fillers, buffers, lubricants, glidants, dyes, disintegrants, odourants, sweeteners, surfactants, mold release agents, antiadhesive agents and coatings. Some excipients may have multiple roles in the compositions, e.g., act as both binders and disintegrants.

Examples of pharmaceutically acceptable disintegrants for oral compositions include starch, pre-gelatinized starch, sodium starch glycolate, sodium carboxymethylcellulose, croscarmellose sodium, microcrystalline cellulose, alginates, resins, surfactants, effervescent compositions, aqueous aluminum silicates and cross-linked polyvinylpyrrolidone.

Examples of pharmaceutically acceptable binders for oral compositions include acacia; cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthane resin, alginates, magnesium-aluminum silicate, polyethylene glycol or bentonite.

Examples of pharmaceutically acceptable fillers for oral compositions include lactose, anhydrolactose, lactose monohydrate, sucrose, dextrose, mannitol, sorbitol, starch, cellulose (particularly microcrystalline cellulose), dihydro- or anhydro-calcium phosphate, calcium carbonate and calcium sulphate.

Examples of pharmaceutically acceptable lubricants useful in the compositions of the invention include magnesium stearate, talc, polyethylene glycol, polymers of ethylene oxide, sodium lauryl sulphate, magnesium lauryl sulphate, sodium oleate, sodium stearyl fumarate, and colloidal silicon dioxide.

Examples of suitable pharmaceutically acceptable odourants for the oral compositions include synthetic aromas and natural aromatic oils such as extracts of oils, flowers, fruits (e.g., banana, apple, sour cherry, peach) and combinations thereof, and similar aromas. Their use depends on many factors, the most important being the organoleptic acceptability for the population that will be taking the pharmaceutical compositions.

Examples of suitable pharmaceutically acceptable dyes for the oral compositions include synthetic and natural dyes such as titanium dioxide, beta-carotene and extracts of grapefruit peel.

Examples of useful pharmaceutically acceptable coatings for the oral compositions, typically used to facilitate swallowing, modify the release properties, improve the appearance, and/or mask the taste of the compositions include hydroxypropylmethylcellulose, hydroxypropylcellulose and acrylate-methacrylate copolymers.

Examples of pharmaceutically acceptable sweeteners for the oral compositions include aspartame, saccharin, saccharin sodium, sodium cyclamate, xylitol, mannitol, sorbitol, lactose and sucrose.

Examples of pharmaceutically acceptable buffers include citric acid, sodium citrate, sodium bicarbonate, dibasic sodium phosphate, magnesium oxide, calcium carbonate and magnesium hydroxide.

Examples of pharmaceutically acceptable surfactants include sodium lauryl sulphate and polysorbates.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

The compounds of the invention may also, for example, be formulated as suppositories e.g., containing conventional suppository bases for use in human or veterinary medicine or as pessaries e.g., containing conventional pessary bases.

The compounds according to the invention may be formulated for topical administration, for use in human and veterinary medicine, in the form of ointments, creams, gels, hydrogels, lotions, solutions, shampoos, powders (including spray or dusting powders), pessaries, tampons, sprays, dips, aerosols, drops (e.g., eye ear or nose drops) or pour-ons.

For application topically to the skin, the agent of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax, sorbitan monostearate, a polyethylene glycol, liquid paraffin, polysorbate 60, cetyl esters wax, cetearyl alcohol, 2-octyldodecanol, benzyl alcohol, and water. Such compositions may also contain other pharmaceutically acceptable excipients, such as polymers, oils, liquid carriers, surfactants, buffers, preservatives, stabilizers, antioxidants, moisturizers, emollients, colourants, and odourants.

Examples of pharmaceutically acceptable polymers suitable for such topical compositions include acrylic polymers; cellulose derivatives, such as carboxymethylcellulose sodium, methylcellulose or hydroxypropylcellulose; natural polymers, such as alginates, tragacanth, pectin, xanthan and cytosan.

Examples of suitable pharmaceutically acceptable oils which are so useful include mineral oils, silicone oils, fatty acids, alcohols, and glycols.

Examples of suitable pharmaceutically acceptable liquid carriers include water, alcohols or glycols such as ethanol, isopropanol, propylene glycol, hexylene glycol, glycerol and polyethylene glycol, or mixtures thereof in which the pseudopolymorph is dissolved or dispersed, optionally with the addition of non-toxic anionic, cationic or non-ionic surfactants, and inorganic or organic buffers.

Examples of pharmaceutically acceptable preservatives include sodium benzoate, ascorbic acid, esters of p-hydroxybenzoic acid and various antibacterial and antifungal agents such as solvents, for example ethanol, propylene glycol, benzyl alcohol, chlorobutanol, quaternary ammonium salts, and parabens (such as methyl paraben, ethyl paraben and propyl paraben).

Examples of pharmaceutically acceptable stabilizers and antioxidants include ethylenediaminetetraacetic acid (EDTA), thiourea, tocopherol and butyl hydroxyanisole.

Examples of pharmaceutically acceptable moisturizers include glycerine, sorbitol, urea and polyethylene glycol.

Examples of pharmaceutically acceptable emollients include mineral oils, isopropyl myristate, and isopropyl palmitate.

The compounds may also be dermally or transdermally administered, for example, by use of a skin patch.

For ophthalmic use, the compounds can be formulated as micronized suspensions in isotonic, pH adjusted, sterile saline, or, preferably, as solutions in isotonic, pH adjusted, sterile saline, optionally in combination with a preservative such as a benzylalkonium chloride.

As indicated, the compounds of the invention can be administered intranasally or by inhalation and is conveniently delivered in the form of a dry powder inhaler or an aerosol spray presentation from a pressurized container, pump, spray or nebulizer with the use of a suitable propellant, e.g., dichlorodifluoromethane, trichlorofluoromethane, dichlorotetrafluoroethane, a hydrofluoroalkane such as 1,1,1,2-tetrafluoroethane (HFA 134AT) or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g., using a mixture of ethanol and the propellant as the solvent, which may additionally contain a lubricant, e.g., sorbitan trioleate.

Capsules and cartridges (made, for example, from gelatin) for use in an inhaler or insufflator may be formulated to contain a powder mix of the compound and a suitable powder base such as lactose or starch.

For topical administration by inhalation the compounds according to the invention may be delivered for use in human or veterinary medicine via a nebulizer.

The pharmaceutical compositions of the invention may contain from 0.01 to 99% weight per volume of the active material. For topical administration, for example, the composition will generally contain from 0.01-10%, more preferably 0.01-1% of the active material.

The active agents can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The pharmaceutical composition or unit dosage form of the invention may be administered according to a dosage and administration regimen defined by routine testing in the light of the guidelines given above in order to obtain optimal activity while minimizing toxicity or side effects for a particular patient. However, such fine tuning of the therapeutic regimen is routine in the light of the guidelines given herein.

The dosage of the active agents of the invention may vary according to a variety of factors such as underlying disease conditions, the individual's condition, weight, gender and age, and the mode of administration. An effective amount for treating a disorder can easily be determined by empirical methods known to those of ordinary skill in the art, for example by establishing a matrix of dosages and frequencies of administration and comparing a group of experimental units or subjects at each point in the matrix. The exact amount to be administered to a patient will vary depending on the state and severity of the disorder and the physical condition of the patient. A measurable amelioration of any symptom or parameter can be determined by a person skilled in the art or reported by the patient to the physician.

The amount of the agent to be administered can range between about 0.01 and about 25 mg/kg/day, preferably between about 0.1 and about 10 mg/kg/day and most preferably between 0.2 and about 5 mg/kg/day. It will be understood that the pharmaceutical formulations of the invention need not necessarily contain the entire amount of the agent that is effective in treating the disorder, as such effective amounts can be reached by administration of a plurality of doses of such pharmaceutical formulations.

In a preferred embodiment of the invention, the compounds according to formula I are formulated in capsules or tablets, preferably containing 10 to 200 mg of the compounds of the invention, and are preferably administered to a patient at a total daily dose of 10 to 300 mg, preferably 20 to 150 mg and most preferably about 50 mg.

A pharmaceutical composition for parenteral administration contains from about 0.01% to about 100% by weight of the active agents of the invention, based upon 100% weight of total pharmaceutical composition.

Generally, transdermal dosage forms contain from about 0.01% to about 100% by weight of the active agents versus 100% total weight of the dosage form.

The pharmaceutical composition or unit dosage form may be administered in a single daily dose, or the total daily dosage may be administered in divided doses. In addition, co-administration or sequential administration of another compound for the treatment of the disorder may be desirable. To this purpose, the combined active principles are formulated into a simple dosage unit.

For combination treatment where the compounds are in separate dosage formulations, the compounds can be administered concurrently, or each can be administered at staggered intervals. For example, the compound of the invention may be administered in the morning and the antimuscarinic compound may be administered in the evening, or vice versa. Additional compounds may be administered at specific intervals too. The order of administration will depend upon a variety of factors including age, weight, gender and medical condition of the patient; the severity and aetiology of the disorders to be treated, the route of administration, the renal and hepatic function of the patient, the treatment history of the patient, and the responsiveness of the patient. Determination of the order of administration may be fine-tuned and such fine-tuning is routine in the light of the guidelines given herein.

DESCRIPTION OF THE INVENTION

Synthesis

Compounds of formula I, and enantiomers, diastereomers, N-oxides, and pharmaceutically acceptable salts thereof, may be prepared by the general methods outlined hereinafter, said methods constituting a further aspect of the invention.

The compounds of this invention can be prepared by employing reactions as shown in the following schemes, in addition to other standard manipulations that are known in the literature, exemplified in the experimental section or clear to one skilled in the art. The starting materials which are not described herein are either commercially available or may be prepared by employing reactions described in the literature or are clear to one skilled in the art. The following examples are provided so that the invention might be more fully understood, are illustrative only, and should not be construed as limiting.

It will be appreciated by those skilled in the art that it may be desirable to use protected derivatives of intermediates used in the preparation of the compounds according to formula I. Protection and deprotection of functional groups may be performed by methods known in the art (see, for example, Green and Wuts Protective *Groups in Organic Synthesis*. John Wiley and Sons, New York, 1999).

The abbreviation PG describes a "protecting group" which is introduced to a reactive group before a certain manipulation is carried out, and which is later removed. Examples of PG's for protecting a reactive group include: acetyl-, trifluoracetyl-, benzoyl-, ethoxycarbonyl-, N-tert-butoxycarbonyl-(BOC), N-benzyloxycarbonyl-(Cbz), benzyl-, methoxybenzyl-, 2,4-dimethoxybenzyl- and for amino groups additionally the phthalyl-group for amino-alkylamino or imino groups; N-methoxynethyl-(MOM), N-benzyloxymethyl-(BOM), N-(trimethylsilyl)ethoxymethyl-(SEM), N-tert-butyl-dimethylsiloxymethyl-, N-tert-butyl-dimethylsilyl-(TBDMS), N-triisopropylsilyl-(TIPS), N-benzyl-, N-4-methoxybenzyl (PMB), N-triphenylmethyl-(Tr), N-tert-butoxycarbonyl-(BOC), N-benzyloxycarbonyl-(Cbz) or N-trimethylsilylethylsulfonyl-(SES) for amide groups; methoxy-, benzyloxy-, trimethylsilyl-(TMS), acetyl-, benzoyl-, tert-butyl-, trityl-, benzyl-, or tetrahydropyranyl (THP) groups for hydroxy groups; or trimethylsilyl-(TMS), methyl-ethyl-, tert-butyl-, benzyl-, or tetrahydropyranyl (THP) groups for carboxyl groups.

In some cases the final product may be further modified, for example by manipulation of substituents. These manipulations may include, but are not limited to, reduction, oxidation, alkylation, acylation, and hydrolysis reactions, which are commonly known to those skilled in the art. In some cases the order of carrying out the foregoing reaction schemes may be varied in order to facilitate the reaction or to avoid unwanted reaction products. The following examples are provided so that the invention might be more fully understood. These examples are illustrative only and should not be constructed as limiting the invention in any way.

The compounds of the invention are generally prepared according to the following scheme, wherein groups $R_1$, $R_2$, $R_3$, and n are as previously defined herein:

Scheme 1.

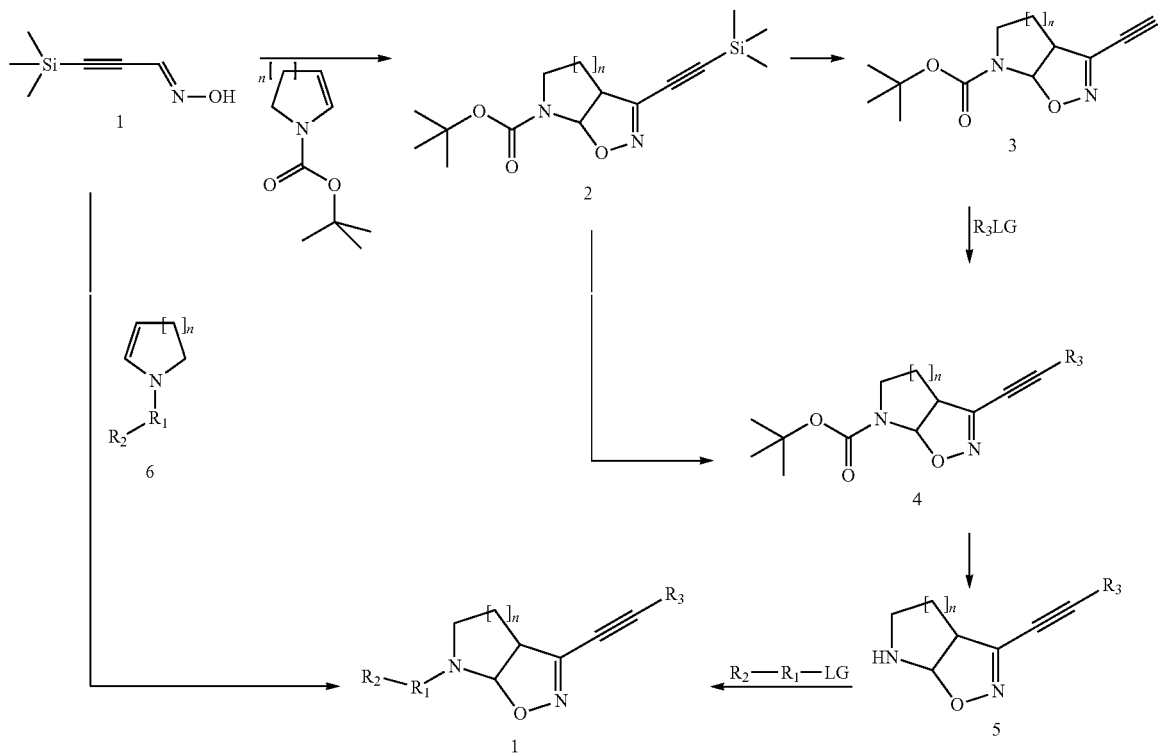

As shown in Scheme 1, silyl protected propargylaldehyde oxime 1 is reacted with N-protected unsaturated cyclic amines through a 1,3-dipolar cycloaddition, with the previous formation of the nitrile oxide species via halogenation-elimination (see e.g. Kanemasa, S.; Nishiuchi, M.; Kamimure, A.; Hori, K. *J. Am. Chem. Soc.* (1994), Vol. 116, pp. 2324). Compounds 2 formed therefrom can be then reacted with an $R_3LG$ compound directly, or by deprotection of the alkyne moiety using standard methodologies (e.g., NaOH or $Na_2CO_3$ in MeOH, or tetrabutylammonium fluoride in THF). LG represents a leaving group such as halogen, mesylate, tosylate, alkylsulphonate, triflate or other without limitation. This reaction is performed e.g. by carrying out a Sonogashira (Chinchilla et al., *Chem. Rev.*, (2007), Vol. 107 (3), pp. 874-922) or like reaction, with the aid of a palladium catalyst and copper iodide. Following N-deprotection by standard methods, reaction with an $R_2$—$R_1$-LG group follows, where LG is as defined above. This last derivatization procedure can be done using standard methods such us e.g. Buchwald reactions, acylation reactions, reaction with alkyl/ arylisocyanates, alkyl/arylchloroformate, chloroformamides, reductive amination, alkylation or any kind of N-derivatization reaction useful to the aim of forming compounds according to formula I and very well known to people skilled in the art. This last reaction can be carried out also by the previous formation of suitable intermediates e.g. a chlorosulphonyl or chlorocarbonyl N-derivative of intermediate 5.

Alternatively, compounds of the invention can be prepared according to Scheme 2:

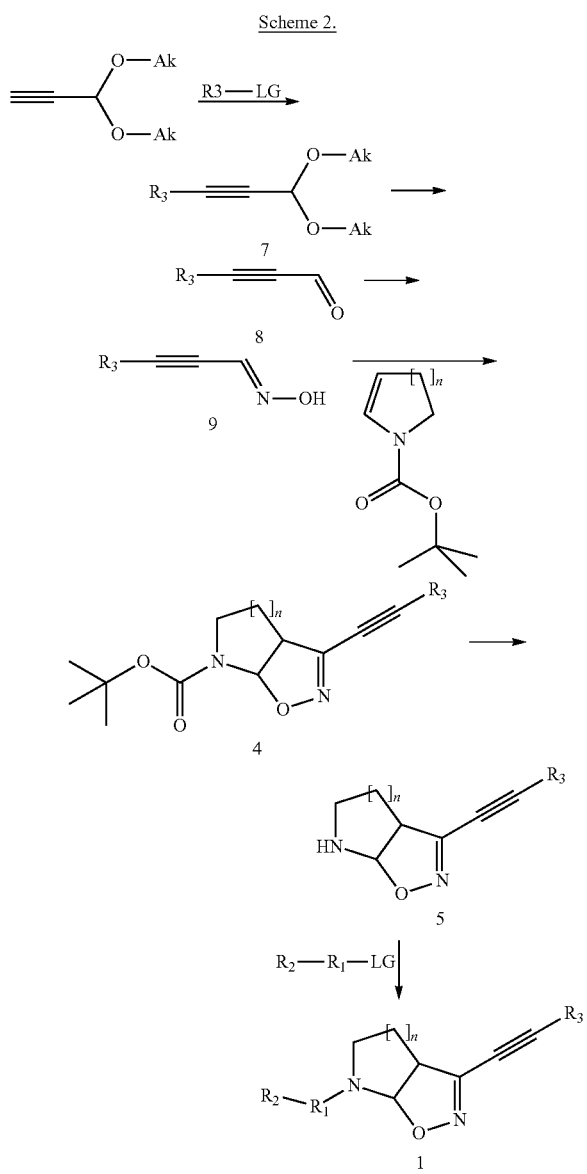

Following Scheme 2, the $R_3$ group is introduced at the beginning of the synthetic pathway by a Sonogashira or Sonogashira-like reaction of the dialkyl or cyclic acetal of propiolaldehyde with the proper alkylating, arylating or derivatising reagent $R_3$-LG where LG is a leaving group as defined above.

The syntheses of other compounds not currently described in the general description above are well documented inside the experimental part of this invention, which follows.

The free bases of compounds according to formula I, their diastereomers or enantiomers can be converted to the corresponding pharmaceutically acceptable salts under standard conditions well known in the art. For example, the free base is dissolved in a suitable organic solvent, such as methanol, treated with, for example one equivalent of maleic or oxalic acid, one or two equivalents of hydrochloric acid or methanesulphonic acid, and then concentrated under vacuum to provide the corresponding pharmaceutically acceptable salt. The residue can then be purified by recrystallization from a suitable organic solvent or organic solvent mixture, such as methanol/diethyl ether.

The N-oxides of compounds according to formula I can be synthesized by simple oxidation procedures well known to those skilled in the art.

Biological Assay

Cell lines stably transfected were generated using inducible expression vectors encoding human $mGlu_5$ receptor using the Tetracycline-Regulated Expression system (T-REx™ system, Invitrogen, Life Technologies). Human $mGluR_5$ open reading frame (ORF), comprehensive of the stop codon, were cloned into the pcDNA4/TO/myc-His™ A vector, carrying the TetO2 sequences. The insertion site was HindIII-PstI for $mGluR_5$ receptors. The obtained constructs were then transfected into the T-REx CHO™ cell line using the FuGENE protocol (Roche); the CHO T-REx™ cell line stably expresses the Tet repressor (from the pcDNA6/TR plasmid) under the selection of blasticidin, 10 μg/ml. Stable clones were obtained selecting with zeocine 1 mg/ml and maintaining in ULTRA CHO medium (LONZA) supplemented with dialyzed FBS, zeocin, blasticidine, at 37° C., in an atmosphere of 5% $CO_2$. The expression of $h-mGluR_5$ receptors was de-repressed with 1 μg/ml tetracycline for 18 h before binding experimentation, while the expression of $h-mGluR_5$ receptors was de-repressed respectively with 3 ng/ml and 10 ng/ml tetracycline for 18 h before calcium fluorescence experimentation.

Radioligand Binding Assay at Native $mGluR_5$ and $mGluR_5$ Receptor Subtypes

Affinity at transmembrane glutamate metabotropic $mGluR_5$ receptor subtypes was evaluated according to the methods of Anderson (Anderson et al., *J Pharmacol. Exp. Ther.*, (2002), Vol. 303(3), pp. 1044-51), with some modifications. Cloned $mGluR_5$ was obtained by re-suspending CHO T-REx $h-mGluR_5$ cells (50 μg/well) in 20 mM HEPES, 2 mM $MgCl_2$, 2 mM $CaCl_2$, pH 7.4, that then were incubated in a final volume of 1 ml for 60 min at 25° C. with 4 nM [$^3$H]MPEP in the absence or presence of competing drugs. Non-specific binding was determined in the presence of 10 mM MPEP. The incubation was stopped by addition of cold Tris buffer pH 7.4 and rapid filtration through 0.2% polyethyleneimine pretreated Filtermat 1204-401 (Perkin Elmer) filters. The filters were then washed with cold buffer and the radioactivity retained on the filters was counted by liquid scintillation spectrometry (Betaplate 1204 BS-Wallac).

Calcium Fluorescence Measurements

Cells were seeded into black-walled, clear-bottom, 96-well plates at a density of 80000 cell/well, in RPMI (without Phenol Red, without L-glutamine; Gibco LifeTechnologies, CA) supplemented with 10% dialyzed FBS. Following 18-h incubation with tetracycline, the cells were loaded with 2 mM $Ca^{2+}$—sensitive fluorescent dye Fluo-4/AM (Molecular Probes) in Hanks' balanced saline solution (HBSS, Gibco LifeTechnologies, CA) with 20 mM Hepes (Sigma) and 2.5 mM probenecid (Sigma), for 1 h at 37° C. The cells were washed three times with HBSS to remove extracellular dye. Fluorescence signals were measured by using the fluorescence microplate reader Flexstation III (Molecular Devices) at sampling intervals of 1.5 s for 60 s.

The antagonist potency was determined using the $EC_{80}$ of the quisqualate used as agonist and the potentiation of $mGlu_5$ activation was determined using the $EC_{20}$ of the agonist (quisqualate or glutamate). The compounds were applied 10 minutes before the application of the agonist. For binding and calcium assay studies, the compounds were dissolved in DMSO or demineralized water according to their solubility. All the reported doses were those of the corresponding salts or bases.

Statistical Analysis.

The inhibition curves of the tested compounds at native and cloned $mGluR_1$ and $mGluR_5$ subtypes were determined by nonlinear regression analysis using software Prism 4.0 (Graphpad, San Diego, Calif.). The $IC_{50}$ values and pseudo-Hill slope coefficients were estimated by the program. The values for the inhibition constant, $K_i$, were calculated according to the equation $K_i = IC_{50}/(1+[L]/K_d)$, where [L] is the concentration of radioligand and $K_d$ is the equilibrium dissociation constant of the radioligand-receptor complex (Cheng et al., *Biochem. Pharmacol.* (1973), Vol. 22, pp. 3099-3108).

Biological data for selected compounds is presented in Table 1.

The invention is illustrated by way of the following examples, in which the following abbreviations may be employed:

AcOH acetic acid
AN acetonitrile
BOC tert-butyloxycarbonyl
conc. concentrated
DCM dichloromethane
DIPEA N,N-diisopropylethylamine
DMF N,N-dimethylformamide
DMSO dimethyl sulfoxide
DPPF 1,1'-bis(diphenyl-phosphino)ferrocene
EI electron ionisation
ESI electrospray ionisation
EtOAc ethyl acetate
EtOH ethanol
HATU 2-(7-aza-1H-benzotriazole-1-yl)-1,1,3,3-tetramethyluronium hexafluorophosphate
HCl hydrochloric acid
HCOOH formic acid

TABLE 1

| Example | h.c. mglu R5 $IC_{50}$ nM | h.c. mgluR5 Calcium $IC_{50}$ nM | $EC_{50}$ nM Glutam. | Fold Increase Glutam. | Fold Increase 1 microM Glutam. | $EC_{50}$ nM Quisq. | Fold Inc. Quisq. | Fold Shift 1 microM Quisq. |
|---|---|---|---|---|---|---|---|---|
| 1 | 3.87 | >1000 | | | | 37.11 | 1.96 | 1.8 |
| 2 | 29.6 | >1000 | | | | | 0 | |
| 3 | 81.5 | 54.76 | | | | | | |
| 4 | 6.99 | | | | | | | |
| 5 | 707.9 | | | | | | 0 | |
| 6 | 24.8 | | 95.18 | 5.1 | 3.24 | 132.15 | 3.3 | 2.7 |
| 6a | | 4875.5 | | | 0.745 | | | |
| 6b | | | 57.01 | 3.98 | 3.62 | | | |
| 7 | 59.2 | 211.8 | | | | 0 | | |
| 8 | 12.52 | >1000 | | | | | | |
| 9 | 15.02 | >1000 | | | | | | |
| 10 | 3.65 | >1000 | | | | 140.7 | 3.5 | 2.2 |
| 11 | 17 | >1000 | | | | | | |
| 12 | 10.6 | | | | | | | |
| 13 | 50.03 | >1000 | | | | 130.7 | 2.06 | 3.2 |
| 14 | 14.8 | >1000 | | | | | | |
| 15 | 21.97 | 21.1 | | | | | | |
| 16 | 151.6 | | | | | | | |
| 17 | >1000 | | | | | | 1.27 | |
| 18 | >1000 | | | | | | | |
| 19 | 239.4 | | | | | | | |
| 20 | >1000 | | | | | | 0 | |
| 21 | | | 0 | 0 | | | | |
| 22 | | | 777 | 4.7 | 3.11 | | | |
| 23 | | | 144 | 2.49 | 4.73 | | | |
| 24 | | | 33.94 | 5.8 | 8.48 | | | |
| 25 | | | 0 | 0 | | | | |
| 26 | | | 54.58 | 5.09 | 2.65 | | | |
| 27 | | | 96.86 | 5.11 | 4.08 | | | |
| 28 | | | 0 | 0 | | | | |
| 29 | | | 0 | 0 | | | | |
| 30 | | | 108.3 | 3.69 | 3.95 | | | |
| 31 | | | 300.8 | 5.29 | 2.14 | | | |
| 32 | | | 1100 | 2.92 | 1.92 | | | |
| 33 | | | | | | | | |
| 34 | | | 541.9 | 3.31 | 5.6 | | | |
| 36 | | | 0 | 0 | | | | |

Preparation of Compounds of the General Formula I

Unless otherwise stated, one or more tautomeric forms of compounds of the examples described hereinafter may be prepared in situ and/or isolated. All tautomeric forms of compounds of the examples described hereinafter should be considered to be disclosed.

HPLC high performance liquid chromatography
HPLC-MS HPLC coupled with mass spectrometry
i.vac. under vacuum
MeOH methanol
MS mass spectrometry MW molecular weight
NaOH sodium hydroxide
NH$_4$OH ammonium hydroxide (30% ammonia in water)
PE petroleum ether
R$_f$ retention value (from thin layer chromatography)
RT room temperature
R.sub.t retention time (from HPLC)
TBTU 2-(1H-benzotriazole-1-yl)-1,1,3,3-tetramethyluronium tetrafluoroborate
THF tetrahydrofurane
TEA triethyl amine
TFA trifluoracetic acid
THF tetrahydrofurane.

The following table (Table 2) illustrates some example compounds of the invention according to general formula I, that were prepared according to Scheme 1 or Scheme 2 accordingly:

Table 2

TABLE 2

| Ex. | Structure | Chemical Name | MF | MW | HPLC-MS (M + H)+ | Ref. Synthesis Scheme |
|---|---|---|---|---|---|---|
| 1 | 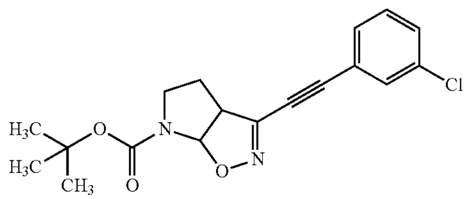 [SMILES: CC(C)(C)OC(=O)N1CCC2C(C#Cc3cccc(Cl)c3)=NOC21] | tert-butyl 3-[2-(3-chlorophenyl)ethynyl]-3a,4,5,6a-tetrahydropyrrolo[3,2-d]isoxazole-6-carboxylate | C$_{18}$H$_{19}$ClN$_2$O$_3$ | 346.80 | 347.11 | 1 |
| 2 | 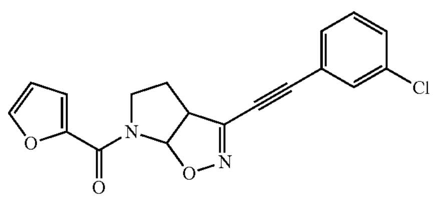 [SMILES: O=C(c1ccco1)N1CCC2C(C#Cc3cccc(Cl)c3)=NOC21] | [3-[2-(3-chlorophenyl)ethynyl]-3a,4,5,6a-tetrahydropyrrolo[3,2-d]isoxazol-6-yl]-(2-furyl)methanone | C$_{18}$H$_{13}$ClN$_2$O$_3$ | 340.76 | 341.77 | 1 |
| 3 | 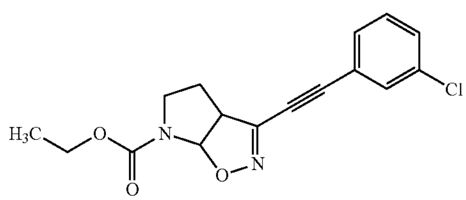 [SMILES: CCOC(=O)N1CCC2C(C#Cc3cccc(Cl)c3)=NOC21] | ethyl 3-[2-(3-chlorophenyl)ethynyl]-3a,4,5,6a-tetrahydropyrrolo[3,2-d]isoxazole-6-carboxylate | C$_{16}$H$_{15}$ClN$_2$O$_3$ | 318.76 | 319.76 | 1 |
| 4 | 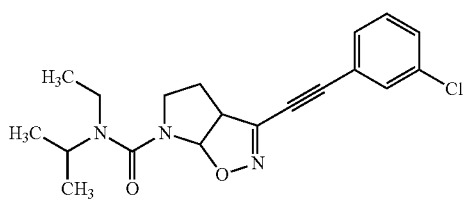 [SMILES: CCN(C(=O)N1CCC2C(C#Cc3cccc(Cl)c3)=NOC21)C(C)C] | 3-[2-(3-chlorophenyl)ethynyl]-N-ethyl-N-isopropyl-3a,4,5,6a-tetrahydropyrrolo[3,2-d]isoxazole-6-carboxamide | C$_{19}$H$_{22}$ClN$_3$O$_2$ | 359.85 | 360.86 | 1 |
| 5 | 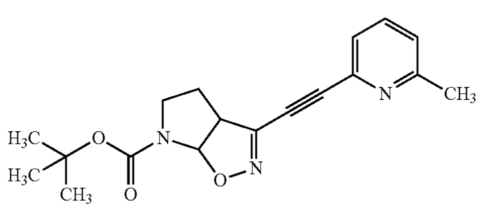 [SMILES: Cc1cccc(C#CC2=NOC3C2CCN3C(=O)OC(C)(C)C)n1] | tert-butyl 3-[2-(6-methyl-2-pyridyl)ethynyl]-3a,4,5,6a-tetrahydropyrrolo[3,2-d]isoxazole-6-carboxylate | C$_{18}$H$_{21}$N$_3$O$_3$ | 327.38 | 328.38 | 2 |
| 6 | 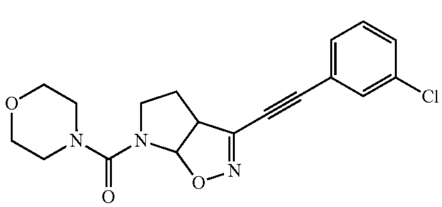 [SMILES: O=C(N1CCOCC1)N1CCC2C(C#Cc3cccc(Cl)c3)=NOC21] | [3-[2-(3-chlorophenyl)ethynyl]-3a,4,5,6a-tetrahydropyrrolo[3,2-d]isoxazol-6-yl]-morpholino-methanone | C$_{18}$H$_{18}$ClN$_3$O$_3$ | 359.81 | 360.81 | 1 |

TABLE 2-continued

| Ex. | Structure | Chemical Name | MF | MW | HPLC-MS (M + H)+ | Ref. Synthesis Scheme |
|---|---|---|---|---|---|---|
| 7 | 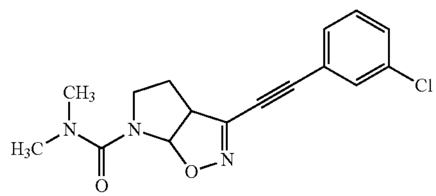 [SMILES: CN(C)C(=O)N1CCC2C(C#Cc3cccc(Cl)c3)=NOC21] | 3-[2-(3-chlorophenyl)ethynyl]-N,N-dimethyl-3a,4,5,6a-tetrahydropyrrolo[3,2-d]isoxazole-6-carboxamide | $C_{16}H_{16}ClN_3O_2$ | 317.77 | 318.78 | 1 |
| 8 | 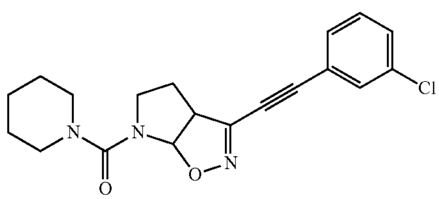 [SMILES: O=C(N1CCCCC1)N1CCC2C(C#Cc3cccc(Cl)c3)=NOC21] | [3-[2-(3-chlorophenyl)ethynyl]-3a,4,5,6a-tetrahydropyrrolo[3,2-d]isoxazol-6-yl]-(1-piperidyl)methanone | $C_{19}H_{20}ClN_3O_2$ | 357.84 | 358.84 | 1 |
| 9 | 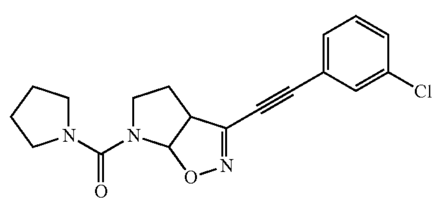 [SMILES: O=C(N1CCCC1)N1CCC2C(C#Cc3cccc(Cl)c3)=NOC21] | [3-[2-(3-chlorophenyl)ethynyl]-3a,4,5,6a-tetrahydropyrrolo[3,2-d]isoxazol-6-yl]-pyrrolidin-1-yl-methanone | $C_{18}H_{18}ClN_3O_2$ | 343.81 | 344.81 | 1 |
| 10 | 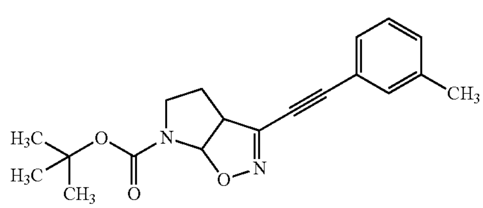 [SMILES: Cc1cccc(C#CC2=NOC3C2CCN3C(=O)OC(C)(C)C)c1] | tert-butyl 3-[2-(m-tolyl)ethynyl]-3a,4,5,6a-tetrahydropyrrolo[3,2-d]isoxazole-6-carboxylate | $C_{19}H_{22}N_2O_3$ | 326.39 | 327.4 | 2 |
| 11 | 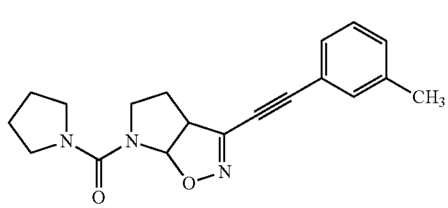 [SMILES: Cc1cccc(C#CC2=NOC3C2CCN3C(=O)N2CCCC2)c1] | [3-[2-(m-tolyl)ethynyl]-3a,4,5,6a-tetrahydropyrrolo[3,2-d]isoxazol-6-yl]-pyrrolidin-1-yl-methanone | $C_{19}H_{21}N_3O_2$ | 323.39 | 324.4 | 2 |
| 12 | 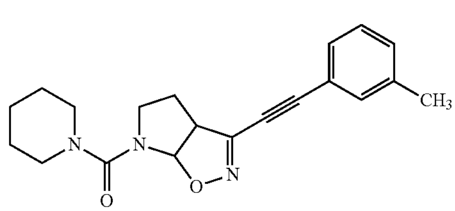 [SMILES: Cc1cccc(C#CC2=NOC3C2CCN3C(=O)N2CCCCC2)c1] | [3-[2-(m-tolyl)ethynyl]-3a,4,5,6a-tetrahydropyrrolo[3,2-d]isoxazol-6-yl]-(1-piperidyl)methanone | $C_{20}H_{23}N_3O_2$ | 337.42 | 338.42 | 2 |
| 13 | 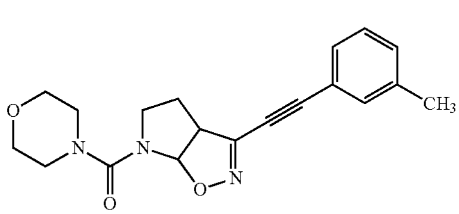 [SMILES: Cc1cccc(C#CC2=NOC3C2CCN3C(=O)N2CCOCC2)c1] | morpholino-[3-[2-(m-tolyl)ethynyl]-3a,4,5,6a-tetrahydropyrrolo[3,2-d]isoxazol-6-yl]methanone | $C_{19}H_{21}N_3O_3$ | 339.39 | 340.4 | 2 |

TABLE 2-continued

| Ex. | Structure | Chemical Name | MF | MW | HPLC-MS (M + H)+ | Ref. Synthesis Scheme |
|---|---|---|---|---|---|---|
| 14 | 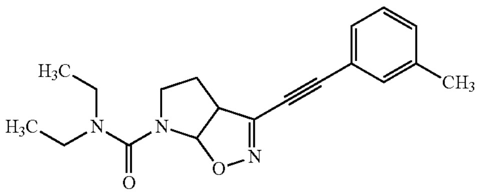 [SMILES: CCN(CC)C(=O)N1CCC2C(C#Cc3cccc(C)c3)=NOC21] | N,N-diethyl-3-[2-(m-tolyl)ethynyl]-3a,4,5,6a-tetrahydropyrrolo[3,2-d]isoxazole-6-carboxamide | $C_{19}H_{23}N_3O_2$ | 325.41 | 326.41 | 2 |
| 15 | 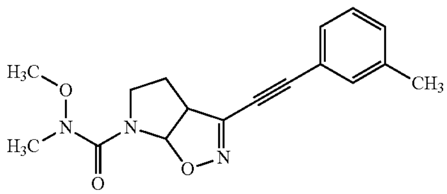 | N-methoxy-N-methyl-3-[2-(m-tolyl)ethynyl]-3a,4,5,6a-tetrahydropyrrolo[3,2-d]isoxazole-6-carboxamide | $C_{17}H_{19}N_3O_3$ | 313.36 | 314.36 | 2 |
| 16 | 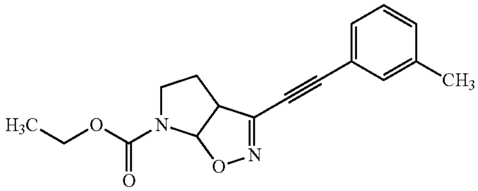 [SMILES: CCOC(=O)N1CCC2C(C#Cc3cccc(C)c3)=NOC21] | ethyl 3-[2-(m-tolyl)ethynyl]-3a,4,5,6a-tetrahydropyrrolo[3,2-d]isoxazole-6-carboxylate | $C_{17}H_{18}N_2O_3$ | 298.34 | 299.34 | 2 |
| 17 | 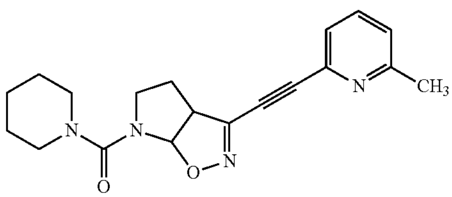 [SMILES: Cc1cccc(C#CC2=NOC3C2CCN3C(=O)N2CCCCC2)n1] | [3-[2-(6-methyl-2-pyridyl)ethynyl]-3a,4,5,6a-tetrahydropyrrolo[3,2-d]isoxazol-6-yl]-(1-piperidyl)methanone | $C_{19}H_{22}N_4O_2$ | 338.41 | 339.42 | 2 |
| 18 | 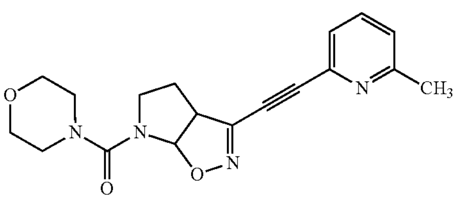 [SMILES: Cc1cccc(C#CC2=NOC3C2CCN3C(=O)N2CCOCC2)n1] | [3-[2-(6-methyl-2-pyridyl)ethynyl]-3a,4,5,6a-tetrahydropyrrolo[3,2-d]isoxazol-6-yl]-morpholino-methanone | $C_{18}H_{20}N_4O_3$ | 340.38 | 341.37 | 2 |
| 19 | 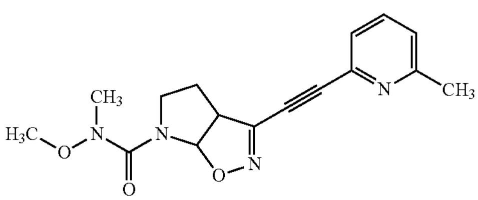 | N-methoxy-N-methyl-3-[2-(6-methyl-2-pyridyl)ethynyl]-3a,4,5,6a-tetrahydropyrrolo[3,2-d]isoxazole-6-carboxamide | $C_{16}H_{18}N_4O_3$ | 314.34 | 315.35 | 2 |
| 20 | 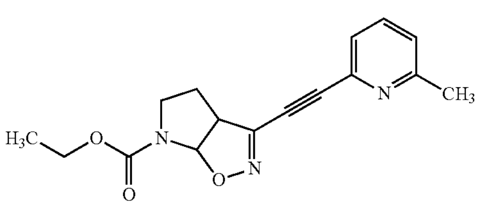 [SMILES: CCOC(=O)N1CCC2C(C#Cc3cccc(C)n3)=NOC21] | ethyl 3-[2-(6-methyl-2-pyridyl)ethynyl]-3a,4,5,6a-tetrahydropyrrolo[3,2-d]isoxazole-6-carboxylate | $C_{16}H_{17}N_3O_3$ | 299.33 | 300.33 | 2 |

$^1$H-NMR data for selected compounds above is shown below in Table 3.

TABLE 3

Selected $^1$H-NMR data

| Ex. | $^1$H-NMR |
|---|---|
| 1 | (400 MHz, DMSO-d6) δ ppm 1.44 (s, 9 H) 2.20 (br. s., 2H) 2.90-3.09 (m, 1H) 3.61-3.71 (m, 1H) 4.15 (br. s., 1H) 6.18-6.37 (m, 1H) 7.45-7.53 (m, 1H) 7.57-7.63 (m, 2H) 7.74 (s, 1H) |
| 2 | (400 MHz, CHLOROFORM-d) δ ppm 2.22 (d, 1H) 2.42 (br. s., 1H) 3.33 (br. s., 1H) 4.11 (br. s., 1H) 4.38 (dd, 1H) 6.56 (dd, 1H) 6.88 (d, 1H) 7.30 (br. s., 1H) 7.32-7.38 (m, 1H) 7.41-7.49 (m, 2H) 7.56 (t, 1H) 7.61 (s, 1H) |
| 3 | (400 MHz, DMSO-d6) δ ppm 1.22 (t, 3H) 2.23 (br. s., 2H) 2.95-3.15 (m, 1H) 3.66-3.76 (m, 1H) 4.05-4.24 (m, 3H) 6.32 (br. s., 1H) 7.46-7.53 (m, 1H) 7.56-7.63 (m, 2H) 7.75 (t, 1H) |
| 4 | (400 MHz, CHLOROFORM-d) δ ppm 1.16 (t, 3H) 1.22 (t, 6H) 2.18 (tt, 1H) 2.29 (dd, 1H) 3.09-3.35 (m, 3H) 3.76 (dd, 1H) 3.92 (t, 1H) 4.13 (spt, 1H) 6.59 (d, 1H) 7.30-7.36 (m, 1H) 7.39-7.46 (m, 2H) 7.54 (t, 1H) |
| 6 | (400 MHz, CHLOROFORM-d) δ ppm 2.10-2.23 (m, 1H) 2.30 (dd, 1H) 3.18 (td, 1H) 3.43-3.50 (m, 4H) 3.73 (m, 4H) 3.87-3.98 (m, 2H) 6.57 (d, 1H) 7.33 (d, 1H) 7.43 (m, 2H) 7.54 (s, 1H) |
| 7 | (400 MHz, CHLOROFORM-d) δ ppm 2.08-2.22 (m, 1H) 2.25-2.34 (m, 1H) 2.96 (s, 6H) 3.25 (td, 1H) 3.80 (dd, 1H) 3.92 (dd, 1H) 6.60 (s, 1H) 7.30-7.37 (m, 1H) 7.38-7.47 (m, 2H) 7.54 (t, 1H) |
| 8 | (400 MHz, CHLOROFORM-d) δ ppm 1.49-1.71 (m, 6H) 2.09-2.22 (m, 1H) 2.23-2.32 (m, 1H) 3.21 (td, 1H) 3.37 (m, 4H) 3.82 (dd, 1H) 3.91 (dd, 1H) 6.61 (d, 1H) 7.33 (dd, 1H) 7.38-7.47 (m, 2H) 7.54 (t, 1H) |
| 9 | (400 MHz, CHLOROFORM-d) δ ppm 1.80-1.98 (m, 4H) 2.11-2.24 (m, 1H) 2.31 (dd, 1H) 3.26 (td, 1H) 3.41-3.49 (m, 2H) 3.49-3.57 (m, 2H) 3.88 (dd, 1H) 3.94 (dd, 1H) 6.62 (d, 1H) 7.33 (dd, 1H) 7.38-7.47 (m, 2H) 7.54 (t, 1H) |
| 10 | (400 MHz, DMSO-d6) δ ppm 1.44 (s, 9 H) 2.09-2.29 (m, 2H) 2.33 (s, 3H) 2.86-3.09 (m, 1H) 3.57-3.72 (m, 1H) 4.14 (br. s., 1H) 6.15-6.37 (m, 1H) 7.30-7.43 (m, 3H) 7.45 (s, 1H) |
| 11 | (400 MHz, CHLOROFORM-d) δ ppm 1.79-1.97 (m, 4H) 2.16 (m, 1H) 2.32 (dd, 1H) 2.37 (s, 3H) 3.26 (td, 1H) 3.40-3.48 (m, 2H) 3.48-3.59 (m, 2H) 3.87 (dd, 1H) 3.93 (dd, 1H) 6.59 (d, 1H) 7.20-7.31 (m, 2H) 7.31-7.40 (m, 2H) |
| 13 | (400 MHz, CHLOROFORM-d) δ ppm 2.16 (m, 1H) 2.33 (dd, 1H) 2.38 (s, 3H) 3.19 (td, 1H) 3.43-3.50 (m, 4H) 3.68-3.77 (m, 4H) 3.86-3.99 (m, 2H) 6.54 (d, 1H) 7.21-7.32 (m, 2H) 7.34-7.41 (m, 2H) |
| 14 | (400 MHz, CHLOROFORM-d) δ ppm 1.19 (t, 6H) 2.10-2.23 (m, 1H) 2.32 (dd, 1H) 2.38 (s, 3H) 3.22 (td, 1H) 3.26-3.43 (m, 4H) 3.79 (dd, 1H) 3.91 (dd, 1H) 6.57 (d, 1H) 7.21-7.31 (m, 2H) 7.33-7.40 (m, 2H) |
| 16 | (400 MHz, DMSO-d6 343 K) δ ppm 1.24 (t, 3H) 2.16-2.25 (m, 2H) 2.35 (s, 3H) 2.99-3.10 (m, 1H) 3.65-3.76 (m, 1H) 4.14 (q, 2H) 4.06-4.31 (m, 1H) 6.30 (d, 1H) 7.28-7.42 (m, 3H) 7.42-7.46 (m, 1H) |
| 17 | (400 MHz, CHLOROFORM-d) δ ppm 1.58-1.70 (m, 6H) 2.08-2.21 (m, 1H) 2.34 (dd, 1H) 2.61 (s, 3H) 3.19 (td, 1H) 3.32-3.43 (m, 4H) 3.81 (dd, 1H) 3.94 (dd, 1H) 6.60 (d, 1H) 7.20 (d, 1H) 7.41 (d, 1H) 7.62 (t, 1H) |
| 18 | (400 MHz, CHLOROFORM-d) δ ppm 2.02-2.22 (m, 1H) 2.35 (dd, 1H) 2.58 (s, 3H) 3.15 (td, 1H) 3.35-3.52 (m, 4H) 3.63-3.78 (m, 4H) 3.86 (dd, 1H) 3.96 (dd, 1H) 6.55 (d, 1H) 7.19 (d, 1H) 7.39 (d, 1H) 7.61 (t, 1H) |
| 19 | (400 MHz, CHLOROFORM-d) δ ppm 2.18 (m, 1H) 2.42 (dd, 1H) 2.63 (s, 3H) 3.15 (s, 3H) 3.34 (td, 1H) 3.69 (s, 3H) 3.90 (dd, 1H) 4.01 (dd, 1H) 6.66 (d, 1H) 7.23 (d, 1H) 7.43 (d, 1H) 7.65 (t, 1H) |
| 20 | (400 MHz, CHLOROFORM-d) δ ppm 1.28-1.38 (m, 3H) 2.11-2.28 (m, 1H) 2.40 (dd, 1H) 2.60 (s, 3H) 3.22 (td, 1H) 3.73-3.93 (m, 1H) 3.93-4.08 (m, 1H) 4.24 (d, 2H) 6.28-6.52 (m, 1H) 7.20 (d, 1H) 7.40 (d, 1H) 7.57-7.66 (m, 1H) |

The following examples illustrate some of the compounds of general formula I as described above. These examples are illustrative only and are not intended to limit the scope of the invention. The reagents and starting materials are readily available to those skilled in the art.

Example 6

3-(3-chlorophenylethynyl)-3a,4,5,6a-tetrahydropyr-rolo[3,2-d]isoxazol-6-yl-(morpholin-4-yl)methanone 1-chloro-3-(3,3-diethoxyprop-1-ynyl)benzene (Intermediate 6a)

A mixture of 1-chloro-3-iodobenzene (4 g, 16.8 mmol), propargylaldehyde diethyl acetal (2.66 mL, 18.5 mmol), bis(trifenilphosphine)palladium(II)dichloride (295 mg, 0.42 mmol), cuprous iodide (160 mg, 0.84 mmol) and triethylamine (60 mL) was stirred at r.t. for 3 h. After 4 h, the reaction mixture was quenched with $H_2O$, extracted with EtOAc, which was washed with brine, dried over $Na_2SO_4$, and evaporated to dryness in vacuo. The residue was purified by automated flash chromatography (Horizon®™—Biotage; Petroleum Ether:EtOAc, 97:3) to give 4 g of the title compound as a fluid yellowish oil. Yield: 100%.

MS: [M+H]$^+$=239.32.

3-(3-chlorophenyl)prop-2-ynal (Intermediate 6b)

To a solution of Intermediate 6a (4 g, 16.7 mmol) in $CH_2Cl_2$ (50 mL) was added 38.8 mL of water and 7.7 mL of trifluoroacetic acid. After 4 h of stirring, a further 4 eq. of trifluoroacetic acid was added. After 24 h the conversion was completed; the 2 layers were separated, the organic layer was washed with water, dried over Na$_2$SO$_4$ and evaporated to dryness in vacuo to afford the title compound as a yellow-brownish oil, used in the next step without further purification.

MS: [M+H]+=165.35.

3-(3-chlorophenyl)prop-2-ynal oxime (Intermediate 6c)

A mixture of 3-chlorophenylpropargylaldehyde (22.8 g, 139 mmol), hydroxylamine hydrochloride (416 mmol, 28.9 g), EtOH (200 mL) and water (50 mL) was stirred at r.t. for 24 h. The reaction mixture was diluted with H$_2$O, extracted with Et$_2$O:EtOAc, washed with brine and evaporated to dryness in vacuo affording 24 g of the title compound (syn:anti 1:1) as a pasty brownish solid. The pale brown residue was used in the next step without further purification.

Yield: 96.4%.
MS: [M+H]+=180.16.

t-butyl-3-(3-chlorophenylethynyl)-3a,4,5,6a-tetrahydropyrrolo[3,2-d]isoxazole-6-carboxylate (Intermediate 6d)

To a solution of Intermediate 6c (20.68 mmol, 3.72 g) in N,N-dimethylformamide (40 mL) was added N-chlorosuccinimide (23.64 mmol, 3.16 g) and the mixture was stirred at room temperature for 2 h. Then water was added and the aqueous layer was extracted with Et$_2$O. The organic phase was dried over Na$_2$SO$_4$, filtered and evaporated. The crude residue was dissolved in CH$_2$Cl$_2$ (40 mL) and cooled at 0° C., then tert-butyl 2,3-dihydropyrrole-1-carboxylate (5.91 mmol, 1 g) followed by TEA (17.73 mmol, 1.79 g, 2.47 mL) were added and the mixture was stirred at room temperature overnight. Afterwards, water was added, the two phases were separated, the organic layer was washed with water and brine, dried over Na$_2$SO$_4$. The solvent was removed in vacuo and the crude residue was purified via automated flash chromatography (Isolera® Biotage, SNAP100 cartidge) eluting with EtOAc:Petroleum Ether gradient from 5% to 50% of EtOAc. The title product (1.1 g) was isolated as a brownish solid.

3-(3-chlorophenylethynyl)-4,5,6,6a-tetrahydropyrrolo[3,2-d]isoxazole (Intermediate 6e)

Into a solution of tert-butyl 3-[2-(3-chlorophenyl)ethynyl]-3a,4,5,6a-tetrahydropyrrolo[3,2-d]isoxazole-6-carboxylate (intermediate 6d, 2.88 mmol, 1 g) in CHCl3 (40 mL) stirred at 0° C. was added dropwise trifluoroacetic acid (28.84 mmol, 3.288 g, 2.208 mL) and the mixture was heated at 60° C. for 5 hours. The reaction was checked by LC/MS showing the correct (M+H)+ peak. The mixture was cooled at 0-5° C. and alkalinized with NaOH to pH=9. Afterwards, water was added, the two phases were separated, the organic layer was washed with water and brine, dried over Na$_2$SO$_4$. The solvent was removed in vacuo affording the title product (0.7 g, 98.4%) as a brown oil that was used for the next step without purification.

3-(3-chlorophenylethynyl)-3a,4,5,6a-tetrahydropyrrolo[3,2-d]isoxazol-6-yl-(morpholin-4-yl)methanone To a solution of 3-(3-chlorophenylethynyl)-4,5,6,6a-tetrahydropyrrolo[3,2-d]isoxazole (intermediate 6e, 0.6 g, 2.4 mmol) in dichloromethane (40 mL) and triethylamine (0.63 mL, 2.8 mmol) was added dropwise 4-morpholinecarbonyl chloride (0.42 mL, 3.6 mmol) and the resulting mixture was stirred overnight at r.t. Afterwards it was heated at 50° C. for 4 h. The reaction mixture was then poured into water, the organic layer was separated, dried over Na$_2$SO$_4$ and evaporated to dryness in vacuo. The crude product was purified by flash chromatography (SP1® Biotage) eluting with a gradient petroleum ether:ethyl acetate 9:1 to 6:4 affording the title compound as a white solid (0.45 g, 51% yield).

$^1$H NMR (400 MHz, CHLOROFORM-d) δ ppm 2.10-2.23 (m, 1H) 2.30 (dd, 1H) 3.18 (td, 1H) 3.43-3.50 (m, 4H) 3.73 (m, 4H) 3.87-3.98 (m, 2H) 6.57 (d, 1H) 7.33 (dd, 1H) 7.43 (m, 2H) 7.54 (s, 1H).

MS: [M+H]$^+$=239.32.

Example 20 ethyl-3-[(6-methyl-2-pyridyl)ethynyl]-3a,4,5,6a-tetrahydropyrrolo[3,2-d]isoxazole-6-carboxylate N-hydroxy-3-trimethylsilyl-prop-2-ynimidoyl chloride (Intermediate 20a)

To a solution of 3-trimethylsilylprop-2-ynal oxime (Carreira, Erick M.; Lohse-Fraefel, Nina, Organic Letters, (2005), Vol. 7, No. 10, pp. 2011-2014, 68 g, 11.9 mmol) in 11.9 mL of DMF stirred at r.t. was added N-chlorosuccinimide (1.99 g, 14.8 mmol). After 4 h stirring, the solution was poured into water and extracted with Et$_2$O. After the usual work-up, the residue (2.09 g) was used as it was for the next step.

t-butyl-3-[(trimethylsilyl)ethynyl]-3a,4,5,6a-tetrahydropyrrolo[3,2-d]isoxazole-6-carboxylate (Intermediate 20b)

A solution of TEA (0.554 mL, 3.85 mmol) in 9.4 mL of dichloromethane was added dropwise into a solution of Compound 20a (1.67 g, 2.57 mmol) and tert-butyl 2,3-dihydropyrrole-1-carboxylate (600 mg, 2.57 mmol) in 42 mL of dichloromethane stirred at 0° C. Afterwards, the reaction mixture was stirred at r.t. for 24 h; then it was diluted with cold water. The organic layer was washed with brine, dried over Na$_2$SO$_4$, evaporated to dryness in vacuo. The crude product was purified by automated flash chromatography (SP1®™—Biotage; gradient Petroleum Ether:EtOAc from 5:5 to 0:10) affording 641 mg of the title product. Yield: 67%.

t-butyl-3-[(6-methylpyridin-2-yl)ethynyl]-3a,4,5,6a-tetrahydro-pyrrolo[3,2-d]isoxazole-6-carboxylate (Intermediate 20c)

To a solution of Intermediate 20b (200 mg, 0.65 mmol) and 2-bromo-6-methylpyridyne (81.1 μl, 0.72 mmol) in N,N-dimethylformamide (4 mL) degassed with a nitrogen stream for 5 min., were added quickly in the order tetrakis (triphenylphosphine)palladium(0) (22.5 mg, 0.02 mmol), tetrabutylammonium fluoride (186 mg, 0.713 mmol) and sodium acetate (106 mg, 1.3 mmol). The mixture was heated in a microwave oven at 120° C. for 10 min. The reaction was poured into water and extracted with ethyl acetate. The organic layer was dried over Na$_2$SO$_4$ and evaporated to dryness. The crude product was purified by automated flash chromatography (SPI®™—Biotage) with a gradient petroleum ether:ethyl acetate from 8:2 to 3:7. The title product was isolated as a brownish oil (212 mg, 54.2%).

3-[(6-methylpyridin-2-yl)ethynyl]-4,5,6,6a-tetrahydropyrrolo[3,2-d]isoxazole (Intermediate 20d)

The title compound was synthesized using the method reported above for Intermediate 6e, but replacing Intermediate 20c for Intermediate 6d. After the usual work-up procedure the residue was purified by means of automated flash chromatography (Horizon®™—Biotage; gradient Petroleum Ether:EtOAc from 98:2 to 9:1) to give the title compound. Yield: 95.9%.

ethyl-3-[(6-methyl-2-pyridyl)ethynyl]-3a,4,5,6a-tetrahydropyrrolo[3,2-d]isoxazole-6-carboxylate To a solution of Intermediate 20d (60 mg, 0.26 mmol) in $CH_2Cl_2$ (6 mL) was added TEA (0.08 mL) and then, dropwise, ethyl chloroformate (38.1 μL, 0.4 mmol). The reaction mixture was stirred at r.t. for 1 h. Afterwards, it was poured into water and extracted with ethyl acetate. The organic layer was dried over $Na_2SO_4$ and evaporated to dryness. The crude product was purified by automated flash chromatography (SP1®™—Biotage) with a gradient petroleum ether:ethyl acetate from 9:1 to 4:6. The title product was isolated as a brownish oil which was further purified by preparative HPLC affording the title product. Yield: 25.3%.

$^1$H NMR (400 MHz, CHLOROFORM-d) δ ppm 1.28-1.38 (m, 3H) 2.11-2.28 (m, 1H) 2.40 (dd, 1H) 2.60 (s, 3H) 3.22 (td, 1H) 3.73-3.93 (m, 1H) 3.93-4.08 (m, 1H) 4.24 (d, 2H) 6.28-6.52 (m, 1H) 7.20 (d, 1H) 7.40 (d, 1H) 7.57-7.66 (m, 1H).

Alternative Procedure for the Synthesis of Intermediate 20c t-butyl-3-ethynyl-3a,4,5,6a-tetrahydropyrrolo[3,2-d]isoxazole-6-carboxylate (Intermediate 20e)

To a solution of Intermediate 20b (530 mg, 1.72 mmol) in MeOH (20 mL) was added $K_2CO_3$ (713 mg, 5.16 mmol) and the mixture was stirred for 1 h at r.t., checked by HPLC-MS, poured into water and extracted with EtOAc. The title compound was obtained by purification with automated flash column chromatography (SP1®™—Biotage) with a gradient petroleum ether:ethyl acetate from 7:3 to 6:4. Colourless oil (406 mg, 49.2%).

t-butyl-3-[(6-methylpyridin-2-yl)ethynyl]-3a,4,5,6a-tetrahydropyrrolo[3,2-d]isoxazole-6-carboxylate (Intermediate 20c)

To a solution of Intermediate 20e (200 mg, 0.85 mmol) and 2-bromo-6-methylpyridyne (106 μl, 0.93 mmol) in N,N-dimethylformamide (4 mL) degassed with a nitrogen stream for 5 min., were added quickly in the order tetrakis (triphenylphosphine)palladium(0) (29.3 mg, 0.025 mmol) and sodium acetate (139 mg, 1.7 mmol) and the mixture was heated in a microwave oven at 120° C. for 10 min. The reaction was poured into water and extracted with ethyl acetate. The organic layer was dried over $Na_2SO_4$ and evaporated to dryness. The crude product was purified by automated flash chromatography (SP1®™—Biotage) with a gradient petroleum ether:ethyl acetate from 8:2 to 3:7. The title product was isolated as a brownish oil (212 mg, 54.2%).

Starting from Intermediate 6e (as hydrochloride) the following compounds were prepared as follows:

Example 21 isopropyl-3-(3-chlorophenylethynyl)-3a,4,5,6a-tetrahydropyrrolo[3,2-d]isoxazole-6-carboxylate Intermediate 6e (30 mg, 0.1 mmol) was dissolved in DCM (0.6 mL) under an argon atmosphere. The reaction mixture was cooled to 0° C. and triethylamine (21 μL, 0.15 mmol) followed by isopropyl chloroformate 1.0 M in toluene (127 μL, 0.12 mmol) were added. Stirring was continued at room temperature overnight. Water was added (5 mL) and the reaction mixture was extracted with DCM (10 mL, 3×). The organic layer was dried over $MgSO_4$ and evaporated to dryness under reduced pressure to give 55 mg of crude product. The crude product was purified by preparative TLC (Hex:EtOAc 6:4), taking up the silica with 5% MeOH in EtOAc. The filtrate was concentrated under vacuum to give 11.4 mg (38% yield) of the title product.

MS: $[M+H]^+$=333.1, $[2M+Na]$=687.3;
$^1$H NMR (400 MHz, DMSO-$d_6$) δ 7.77-7.73 (m, 1H), 7.63-7.57 (m, 2H), 7.53-7.47 (m, 1H), 6.35-6.26 (m, 1H), 4.89-4.78 (m, 1H), 4.21-4.12 (m, 1H), 3.73-3.65 (m, 1H), 3.08-2.97 (m, 1H), 2.26-2.18 (m, 2H), 1.23 (d, 6H).

Example 22 cyclopropylmethyl-3-(3-chlorophenylethynyl)-3a,4,5,6a-tetrahydropyrrolo[3,2-d]isoxazole-6-carboxylate Intermediate 6e (30 mg, 0.1 mmol) was dissolved in DCM (0.6 mL) under an argon atmosphere. The reaction mixture was cooled to 0° C. and triethylamine (21 μL, 0.15 mmol) followed by cyclopropylmethyl chloroformate (17 mg, 0.12 mmol)) were added. Stirring was continued at room temperature overnight. Water was added (5 mL) and the reaction mixture was extracted with DCM (10 mL, 3×). The organic layer was dried over $MgSO_4$, and evaporated to dryness under reduced pressure to give 48 mg of crude product. The crude product was purified by preparative TLC (Hex:EtOAc 4:6), taking up the silica with 5% MeOH in EtOAc. The filtrate was concentrated under vacuum to give 18.6 mg (50% yield) of the title product.

MS: $[M+H]^+$=345.8
$^1$H NMR (400 MHz, DMSO-$d_6$) δ 7.77-7.74 (m, 1H), 7.64-7.56 (m, 2H), 7.51 (dd, 1H), 6.33 (d, 1H), 4.23-4.11 (m, 2H), 3.76-3.67 (m, 1H), 3.14-2.97 (m, 2H), 2.29-2.16 (m, 2H), 1.21-1.07 (m, 1H), 0.53 (d, 2H), 0.35-0.26 (m, 2H).

Example 23 cyclopentyl-3-(3-chlorophenylethynyl)-3a,4,5,6a-tetrahydropyrrolo[3,2-d]isoxazole-6-carboxylate Intermediate 6e (30 mg, 0.11 mmol) was dissolved in DCM (0.6 mL) under an argon atmosphere. The reaction mixture was cooled to 0° C. and triethylamine (21 μL, 0.15 mmol)) followed by cyclopentyl chloroformate (16 μL, 0.13 mmol) were added. Stirring was continued for 1 hour at room temperature. Water was added (5 mL) and the reaction mixture was extracted with EtOAc (10 mL, 3×). The organic layer was dried over $Na_2SO_4$, and evaporated to dryness under reduced pressure to give 54 mg of crude product. The crude product was purified by flash column chromatography on silica using EtOAc:DCM:Hex 3:1:1 as an eluent. 27 mg of the title compound as a yellow thick oil was obtained (71% yield).

MS: [2M+Na]=739.4

$^1$H NMR (400 MHz, DMSO-d6) δ 7.78-7.73 (m, 1H), 7.63-7.57 (m, 2H), 7.53-7.47 (m, 1H), 6.29 (dd, 1H), 5.05 (s, 1H), 4.26-4.11 (m, 1H), 3.73-3.62 (m, 1H), 3.14-2.95 (m, 1H), 2.27-2.15 (m, 2H), 1.90-1.75 (m, 2H), 1.75-1.50 (m, 6H).

Example 24

2,2-dimethylpropyl-3-(3-chlorophenylethynyl)-3a,4,5,6a-tetrahydropvrrolo[3,2-d]isoxazole-6-carboxylate Intermediate 6e (30 mg, 0.11 mmol) was dissolved in DCM (0.6 mL) under an argon atmosphere. The reaction mixture was cooled to 0° C. and triethylamine (21 µL, 0.15 mmol) followed by neopentyl chloroformate (19 µL, 0.13 mmol) were added. Stirring was continued for 1 hour at room temperature. Water was added (5 mL) and the reaction mixture was extracted with EtOAc (10 mL, 4×). The organic layer was dried over Na$_2$SO$_4$, and evaporated to dryness under reduced pressure to give 48 mg of crude product. The crude product was purified by flash column chromatography on silica using EtOAc:DCM:Hex 3:1:1 as an eluent. 33 mg of the title compound as a yellow thick oil was obtained (86% yield).

MS: [2M+Na]=743.6

$^1$H NMR (400 MHz, DMSO-d6) δ 7.76 (s, 1H), 7.66-7.56 (m, 2H), 7.54-7.45 (m, 1H), 6.40-6.26 (m, 1H), 4.28-4.10 (m, 1H), 3.89-3.62 (m, 3H), 3.22-2.95 (m, 1H), 2.24 (s, 2H), 0.97-0.90 (m, 9H).

Example 25

3-(3-chlorophenylethynyl)-N-(propan-2-yl)-3a,4,5,6a-tetrahydropyrrolo[3,2-d]isoxazole-6-carboxamide Intermediate 6e (30 mg, 1.1 mmol) was dissolved in DCM (0.45 mL) under an argon atmosphere. The reaction mixture was cooled to 0° C. and triethylamine (32 µL, 0.23 mmol)) followed by isopropyl isocyanate (10 µL, 0.11 mmol) were added. Stirring was continued for 24 hours at room temperature. Water was added (5 mL) and the reaction mixture was extracted with DCM (10 mL, 3×). The organic layer was dried over MgSO$_4$ and evaporated to dryness under reduced pressure to give 41 mg of crude product. The residue was purified via preparative HPLC to afford 23 mg of the title compound (66% yield).

MS: [M+H]$^+$=332.1

$^1$H NMR (400 MHz, DMSO-d6) δ 7.75 (t, 1H), 7.63-7.56 (m, 2H), 7.53-7.46 (m, 1H), 6.44 (d, 1H), 6.35 (d, 1H), 4.14-4.06 (m, 1H), 3.84-3.75 (m, 1H), 3.70-3.61 (m, 1H), 3.00-2.89 (m, 1H), 2.24-2.10 (m, 2H), 1.09 (dd, 6H).

Example 26

N-t-butyl-3-(3-chlorophenylethynyl)-3a,4,5,6a-tetrahydropyrrolo[3,2-d]isoxazole-6-carboxamide Intermediate 6e (30 mg, 0.1 mmol) was dissolved in DCM (0.45 mL) under an argon atmosphere. The reaction mixture was cooled to 0° C. and triethylamine (49 µL, 0.35 mmol) followed by tert-butyl isocyanate (17 µL, 0.14 mmol) were added. Stirring was continued for 24 hours at room temperature. Water was added (5 mL) and the reaction mixture was extracted with DCM (10 mL, 3×). The organic layer was dried over MgSO$_4$ and evaporated to dryness under reduced pressure to give 45 mg of crude product. The residue was purified via flash column chromatography on silica eluting with AcOEt:Hex 1:1. The collected combined fractions were taken up with hexane and finally purified via preparative TLC (AcOEt:Hex 1:9), taking up the silica with 5% MeOH in EtOAc. The filtrate was concentrated under vacuum to give 14 mg (33% yield) of the title product.

MS: [M+H]$^+$=346

$^1$H NMR (400 MHz, DMSO-d6) δ 7.75 (t, 1H), 7.62-7.57 (m, 2H), 7.53-7.47 (m, 1H), 6.48 (d, 1H), 5.82 (s, 1H), 4.14-4.05 (m, 1H), 3.69-3.60 (m, 1H), 3.03-2.90 (m, 1H), 2.22-2.11 (m, 2H), 1.29 (s, 9H).

Example 27

3-(3-chlorophenylethynyl)-N-cyclopentyl-3a,4,5,6a-tetrahydropyrrolo[3,2-d]isoxazole-6-carboxamide Intermediate 6e (30 mg, 0.1 mmol) was dissolved in DCM (0.45 mL) under an argon atmosphere. The reaction mixture was cooled to 0° C. and triethylamine (35 µL, 0.25 mmol) followed by cyclopentyl isocyanate (14 µL, 0.12 mmol) were added. Stirring was continued for 24 hours at room temperature. Water was added (5 mL) and the reaction mixture was extracted with DCM (10 mL, 3×). The organic layer was dried over MgSO$_4$ and evaporated to dryness under reduced pressure to give 48 mg of crude product. The crude product was purified via flash column chromatography on silica eluting with a gradient from Hex:EtOAc 9:1 to EtOAc. The collected combined fractions were evaporated to dryness, taken up with hexane, purified by preparative TLC (Hex:EtOAc 9:1) and finally by preparative HPLC to afford 14 mg (36% yield) of the title product.

MS:[M+H]$^+$=358.1

$^1$H NMR (400 MHz, DMSO-d6) δ 7.77-7.73 (m, 1H), 7.59 (m, 2H), 7.53-7.46 (m, 1H), 6.46 (d, 1H), 6.41 (d, 1H), 4.10 (t, 1H), 4.00-3.88 (m, 1H), 3.71-3.62 (m, 1H), 3.00-2.89 (m, 1H), 2.23-2.09 (m, 2H), 1.86-1.74 (m, 2H), 1.68-1.60 (m, 2H), 1.53-1.37 (m, 4H).

Example 28

3-(3-chlorophenyl)ethynyl)-3a,4,5,6a-tetrahydropyrrolo[3,2-d]isoxazol-6-yl-(furan-3-yl)methanone Intermediate 6e (30 mg, 0.1 mmol) was dissolved in DCM (0.6 mL) under an argon atmosphere. The reaction mixture was cooled to 0° C. and triethylamine (21 µL, 0.14 mmol) followed by furan-3-carbonyl chloride (17 mg, 0.12 mmol) were added. Stirring was continued at room temperature overnight. Water was added (5 mL) and the reaction mixture was extracted with DCM (10 mL, 3×). The organic layer was dried over MgSO$_4$, and evaporated to dryness under reduced pressure to give 53 mg of crude product. The crude product was purified by flash column chromatography on silica followed by preparative TLC (Hex:EtOAc 2:8) taking up the silica with 5% MeOH in EtOAc. The filtrate was evaporated under vacuum to give 22.4 mg of the title product (62% yield).

MS: [M+H]+=341.5

$^1$H NMR (400 MHz, DMSO) δ 8.30-8.14 (m, 1H), 7.86-7.74 (m, 2H), 7.66-7.57 (m, 2H), 7.51 (t, 1H), 6.85-

6.78 (m, 1H), 6.69-6.54 (m, 1H), 4.36-4.07 (m, 2H), 3.14-2.98 (m, 1H), 2.38-2.15 (m, 2H).

Example 29

3-(3-chlorophenylethynyl)-3a,4,5,6a-tetrahydropyrrolo[3,2-d]isoxazol-6-yl-(5-methylfuran-2-yl)methanone Intermediate 6e (30 mg, 0.1 mmol) was dissolved in DCM (0.6 mL) under an argon atmosphere. The reaction mixture was cooled to 0° C. and triethylamine (21 µL, 0.14 mmol) followed by 5-methylfuran-2-carbonyl chloride (18 mg, 0.13 mmol) were added. Stirring was continued for 1 hour at room temperature. Water was added (5 mL) and the reaction mixture was extracted with EtOAc (10 mL, 3×). The organic layer was dried over $Na_2SO_4$ and evaporated to dryness under reduced pressure to give 50 mg of crude product. The crude product was purified by flash column chromatography on silica using EtOAc:DCM:Hex 3:1:1 as an eluent. 30 mg of the title compound as a yellow thick oil was obtained (80% yield).

MS: $[M+H]^+$=355.1, $[2M+Na]$=731.4

$^1$H NMR (400 MHz, DMSO-d6) δ 7.78 (t, 1H), 7.66-7.56 (m, 2H), 7.55-7.46 (m, 1H), 7.11 (d, 1H), 6.81 (s, 1H), 6.33 (dd, 1H), 4.30 (s, 1H), 4.21-3.86 (m, 2H), 3.08 (s, 1H), 2.36 (s, 3H), 2.30 (s, 1H).

Example 30

3-(3-chlorophenylethynyl)-3a,4,5,6a-tetrahydropyrrolo[3,2-d]isoxazol-6-yl-(cyclopentyl)methanone Intermediate 6e (30 mg, 0.1 mmol) was dissolved in DCM (0.6 mL) under an argon atmosphere. The reaction mixture was cooled to 0° C. and triethylamine (37 µL, 0.26 mmol) followed by cyclopentanecarbonyl chloride (15 µL, 0.13 mmol) were added. Stirring was continued for 1 hour at room temperature. Water was added (5 mL) and reaction mixture was extracted with DCM (10 mL, 3×). The organic layer was dried over $MgSO_4$, and evaporated to dryness under reduced pressure to give 46 mg of crude product. The crude product was purified by flash column chromatography on silica using hexane:EtOAc 7:3 as an eluent to afford 35 mg of the title product (96% yield).

MS: $[M+H]^+$=343.1

$^1$H NMR (400 MHz, DMSO-d6, mixture of rotamers) δ 7.78-7.75 (m, 1H), 7.64-7.58 (m, 2H), 7.50 (t, 1H), 6.60 (d, $1H_{major\ rotamer}$), 6.45 (d, $1H_{minor\ rotamer}$), 4.28 (t, $1H_{major\ rotamer}$), 4.13 (t, $1H_{minor\ rotamer}$), 3.92-3.82 (m, 1H), 3.24-3.14 (m, $1H_{major\ rotamer}$), 3.09-3.00 (m, $1H_{minor\ rotamer}$), 2.99-2.87 (m, 1H), 2.29-2.11 (m, 2H), 1.93-1.77 (m, 2H), 1.73-1.52 (m, 6H).

Example 31

3-(3-chlorophenylethynyl)-3a,4,5,6a-tetrahydropyrro[3,5,6a-tetrahdrorrolo3,2-d]oxazol-6-yl-(oxan-4-yl)methanone Intermediate 6e (30 mg, 0.1 mmol) was dissolved in DCM (0.6 mL) under an argon atmosphere. The reaction mixture was cooled to 0° C. and triethylamine (37 µL, 0.26 mmol) followed by tetrahydro-2H-pyran-4-carbonyl chloride (19 mg, 0.13 mmol) were added. Stirring was continued for 1 hour at room temperature. Water was added (5 mL) and reaction mixture was extracted with DCM (10 mL, 3×). The organic layer was dried over $MgSO_4$, and evaporated to dryness under reduced pressure to give 65 mg of crude product. The crude product was purified by flash column chromatography on silica using a gradient DCM:EtOAc 8:2 to 6:4 as an eluent. 32 mg of the title compound were obtained (84% yield).

MS:$[M+H]^+$=359.1

$^1$H NMR (400 MHz, DMSO-d6, mixture of rotamers) δ 7.78-7.75 (m, 1H), 7.64-7.57 (m, 1H), 7.51 (t, 1H), 6.67 (d, $1H_{major\ rotamer}$), 6.46 (d, $1H_{minor\ rotamer}$), 4.29 (t, $1H_{major\ rotamer}$), 4.13 (t, $1H_{minor\ rotamer}$), 3.94-3.77 (m, 4H), 3.44-3.33 (m, 3H), 3.00-2.87 (m, 1H), 2.35-2.08 (m, 2H), 1.71-1.52 (m, 4H).

Example 32

3-(3-chlorophenylethynyl)-3a,4,5,6a-tetrahydropyrrolo[3,2-d]isoxazol-6-yl-(4-methylpiperazin-1-yl)methanone Intermediate 6e (30 mg, 0.1 mmol) was dissolved in DCM (0.6 mL) under an argon atmosphere. The reaction mixture was cooled to 0° C. and triethylamine (37 µL, 0.26 mmol) followed by 4-methyl-1-piperazinecarbonyl chloride (17 µL, 0.13 mmol) were added. Stirring was continued for 1 hour at room temperature. Water was added (5 mL) and reaction mixture was extracted with DCM (10 mL, 3×). The organic layer was dried over $MgSO_4$ and evaporated to dryness under reduced pressure to give 42 mg of crude product. The crude product was purified by flash column chromatography on silica using DCM:MeOH 19:1 as an eluent. 20 mg of the title product were obtained (51% yield).

MS: $[M+H]^+$=373.3

$^1$H NMR (400 MHz, DMSO-d6) δ 7.77-7.73 (m, 1H), 7.62-7.57 (m, 2H), 7.53-7.46 (m, 1H), 6.52 (d, 1H), 4.12 (t, 1H), 3.59 (dd, 1H), 3.36-3.28 (m, 2H, the signal is partially covered by water), 3.28-3.19 (m, 2H), 3.16-3.07 (m, 1H), 2.36-2.24 (m, 4H), 2.23-2.16 (m, 4H), 2.15-2.05 (m, 1H).

Example 33

4-oxanyl-3-(3-chlorophenylethynyl)-3a,4,5,6a-tetrahydropyrrolo[3,2-d]isoxazole-6-carboxylate Intermediate 6e (30 mg, 0.11 mmol) was dissolved in DCM (0.6 mL) under an argon atmosphere. The reaction mixture was cooled to 0° C. and triethylamine (21 µL, 15 mmol) followed by oxan-4-yl chloroformate (21 mg, 0.13 mmol) were added. Stirring was continued for 1.5 hour at room temperature. Water was added (5 mL) and reaction mixture was extracted with EtOAc (10 mL, 3×). The organic layer was dried over $Na_2SO_4$ and evaporated to dryness under reduced pressure to give 60 mg of crude product. The crude product was purified by flash column chromatography on silica using EtOAc:DCM 3:1 as an eluent. After a further flash purification 28 mg of the title compound as a yellow thick oil were obtained (70% yield).

MS: $[2M+Na]^+$=771.3

$^1$H NMR (400 MHz, DMSO-d6) δ 7.75 (s, 1H), 7.65-7.56 (m, 2H), 7.53-7.47 (m, 1H), 6.35 (t, 1H), 4.83 (s, 1H), 4.20 (s, 1H), 3.87-3.63 (m, 3H), 3.50 (d, 2H), 3.05 (s, 1H), 2.24 (s, 2H), 1.87 (s, 2H), 1.59 (s, 2H).

Example 34

3-methylbutyl-3-(3-chlorophenylethynyl)-3a,4,5,6a-tetrahydropyrrolo[3,2-d]isoxazole-6-carboxylate Intermediate 6e (30 mg, 0.11 mmol) was dissolved in DCM (0.6 mL) under an argon atmosphere. The reaction mixture was cooled to 0° C. and triethylamine (21 μL, 0.15 mmol) followed by 3-methylbutyl chloroformate (19 mg, 0.13 mmol) were added. Stirring was continued for 1 hour at room temperature. Water was added (5 mL) and reaction mixture was extracted with EtOAc (10 mL, 3×). The organic layer was dried over $Na_2SO_4$, and evaporated to dryness under reduced pressure to give 53 mg of crude product. The crude product was purified by column chromatography on silica using EtOAc:DCM 3:1 as an eluent. 34 mg of the title product as a yellow thick oil was obtained (89% yield).

MS: $[2M+Na]^+$=743.3

$^1$H NMR (400 MHz, DMSO-d6) δ 7.76 (s, 1H), 7.64-7.56 (m, 2H), 7.55-7.46 (m, 1H), 6.37-6.23 (m, 1H), 4.24-4.14 (m, 1H), 4.16-4.05 (m, 2H), 3.77-3.61 (m, 1H), 3.12-2.97 (m, 1H), 2.22 (m, 2H), 1.79-1.58 (m, 1H), 1.49 (dt, 2H), 0.91 (d, 6H).

Example 35

3-(3-chlorophenylethynyl)-N-(pentan-3-yl)-3a,4,5,6a-tetrahydropyrrolo[3,2-d]isoxazole-6-carboxamide Intermediate 6e (40 mg, 0.14 mmol) was dissolved in DCM (0.45 mL) under an argon atmosphere. The reaction mixture was cooled to 0° C. and triethylamine (54 μL, 0.038 mmol) followed by 2-ethylpropylisocyanate (18 mg, 0.15 mmol) were added. Stirring was continued for 24 hours at room temperature. Water was added (5 mL) and reaction mixture was extracted with DCM (10 mL, 3×). The organic layer was dried over $MgSO_4$ and evaporated to dryness under reduced pressure to give 57 mg of crude product. The crude product was purified via preparative HPLC to afford 42 mg of the title product (78% yield).

MS: $[M+H]^+$=360.0

$^1$H NMR (400 MHz, DMSO-d6) δ 7.75 (t, 1H), 7.63-7.56 (m, 2H), 7.54-7.46 (m, 1H), 6.48 (d, 1H), 6.19 (d, 1H), 4.17-4.07 (m, 1H), 3.73-3.62 (m, 1H), 3.50-3.41 (m, 1H), 3.03-2.92 (m, 1H), 2.24-2.13 (m, 2H), 1.52-1.31 (m, 4H), 0.83 (td, 6H).

Example 36

3-(3-chlorophenylethynyl)-N-(pyridin-3-yl)-3a,4,5,6a-tetrahydropyrrolo[3,2-d]isoxazole-6-carboxamide Intermediate 6e (40 mg, 0.14 mmol) was dissolved in DCM (0.8 mL) under an argon atmosphere. The reaction mixture was cooled to 0° C. and triethylamine (47 μL, 0.33 mmol) followed by pyridine-3-isocyanate (19 mg, 0.15 mmol) were added. Stirring was continued for 24 hours at room temperature. Water was added (5 mL) and reaction mixture was extracted with DCM (10 ml, 3×). The organic layer was dried over $MgSO_4$, and evaporated to dryness under reduced pressure to give 61 mg of crude product. The crude product was purified via flash column chromatography on silica with a gradient hexane to Hex:EtOAc 1:1 as eluent. The combined collected fractions were evaporated to dryness and further purified by preparative TLC (Hex:EtOAc 6:4). 40 mg of the title compound were obtained (77% yield).

MS: $[M+H]^+$=367.2, $[2M+Na]^+$=755.2

$^1$H NMR (400 MHz, DMSO-d6) δ 8.86 (s, 1H), 8.70 (d, 1H), 8.22 (dd, 1H), 7.94 (ddd, 1H), 7.77 (t, 1H), 7.65-7.58 (m, 2H), 7.55-7.48 (m, 1H), 7.32 (dd, 1H), 6.60 (d, 1H), 4.24 (t, 1H), 3.91-3.82 (m, 1H), 3.21-3.10 (m, 1H), 2.37-2.24 (m, 2H).

Example 37

3-(3-chlorophenylethynyl)-N-(2,2-dimethylpropyl)-3a,4,5,6a-tetrahydropyrrolo[3,2-d]isoxazole-6-carboxamide Intermediate 6e (30 mg, 0.1 mmol) was dissolved in DCM (0.45 mL) under an argon atmosphere. The reaction mixture was cooled to 0° C. and triethylamine (32 μL, 0.24 mmol) followed by 2,2-dimethylpropyl isocyanate (12 mg, 0.1 mmol) were added. Stirring was continued for 24 hours at room temperature. Water was added (5 mL) and the reaction mixture was extracted with DCM (10 ml, 3×). The organic layer was dried over $MgSO_4$ and evaporated to, dryness under reduced pressure to give 39 mg of crude product. The crude product was purified via preparative HPLC to yield 23 mg of the title product (60%).

MS: $[M+H]^+$=360.2

$^1$H NMR (400 MHz, DMSO-d6) δ 7.75 (t, 1H), 7.63-7.56 (m, 2H), 7.53-7.47 (m, 1H), 6.53-6.45 (m, 2H), 4.16-4.09 (m, 1H), 3.71-3.64 (m, 1H), 3.07-2.96 (m, 2H), 2.78 (dd, 1H), 2.23-2.16 (m, 2H), 0.84 (s, 9H).

Example 38

3-(3-chlorophenylethynyl)-3a,4,5,6a-tetrahydropyrrolo[3,2-d]isoxazol-6-yl-(1,5-dimethyl-1H-pyrazol-3-yl)methanone Intermediate 6e (50 mg, 0.18 mmol) was suspended in DCM (1 mL) at room temperature. TEA (52 μl, 37 mmol) was added and the suspension became a clear, yellow solution. 1,5-dimethyl-1H-pyrazole-3-carbonyl chloride (28 mg, 18 mmol) as solid was added. The reaction solution was stirred at room temperature for 2 h. The solvent was removed in vacuo. The by-products were removed by dissolving the crude product in MeOH and precipitating with $Et_2O$. Afterwards, the solvents were removed in vacuo and the residue was dissolved in 10 mL of EtOAc and washed three times with 1M $KHSO_4$ to give the desired product (34 mg, 53% yield).

MS:$[M+H]^+$=369.1, $[2M+H]^+$=759.2

$^1$H NMR (400 MHz, DMSO-d6) δ 7.77 (t, 1H), 7.66-7.56 (m, 2H), 7.50 (t, 1H), 7.34 (d, 1H), 6.50 (d, 1H), 4.30 (t, 1H), 4.01 (dd, 1H), 3.80 (d, 3H), 3.06 (td, 1H), 2.36-2.10 (m, 5H).

Example 39

3-(3-chlorophenlethynyl)-3a,4,5,6a-tetrahydropyrrolo[3,2-d]isoxazol-6-yl-(thiazol-4-yl)methanone Intermediate 6e (50 mg, 18 mmol)) was suspended in DCM (1 mL) at room temperature. TEA (52 μl, 0.37 mmol)) was added and the suspension became a clear, yellow solution. Next, 1,3-thiazole-4-carbonyl chloride (26 mg, 0.18 mmol) as a solid was added. The reaction solution was stirred at room temperature for 2 h. The solvent was removed in vacuo and the crude product was purified using flash column chromatography Hex:EtOAc 1:1, $TLC_{Rf}$=0.24). Trituration with $Et_2O$ increased the product purity from 91% to 93%. The final purification step was performed on the prep. HPLC, which yielded 11 mg of the desired product (as formate salt) with a purity of 99.7% (17% yield).

MS: [M+H]$^+$=358.1

$^1$H NMR (400 MHz, DMSO-d6) δ 9.30-9.16 (m, 1H), 8.44 (d, 1H), 7.78 (t, 1H), 7.61 (tt, 2H), 7.55-7.45 (m, 1H), 7.35 (d, 1H), 4.34-4.23 (d, 1H), 4.03 (dd, 1H), 3.15 (dd, 1H), 2.32-2.22 (m, 2H).

Example 40

3-(3-chlorophenylethynyl)-3a,4,5,6a-tetrahydropyrrolo[3,2-d]isoxazol-6-yl-(4,4-difluorocyclohexyl) methanone Intermediate 6e (30 mg, 0.11 mmol) was dissolved in DCM (0.6 mL) under an argon atmosphere. The reaction mixture was cooled to 0° C. and triethylamine (37 µL, 26 mmol) followed by 4,4-difluorocyclohexane-1-carbonyl chloride (23 mg, 0.13 mmol) were added. Stirring was continued at room temperature overnight. Water was added (5 mL) and the reaction mixture was extracted with DCM (10 mL, 3×). The organic layer was extracted with brine and evaporated to dryness under reduced pressure. The crude product was purified by flash column chromatography on silica using DCM:MeOH 95:5 as an eluent to give 38.0 mg. The obtained product was further purified by preparative TLC, using as an eluent AcOEt:hexane (1:1) and finally by preparative HPLC to give 17 mg of the title compound (41% yield).

MS: [2M+Na]+=807.3

$^1$H NMR (400 MHz, DMSO-d6) δ 7.78-7.75 (m, 1H), 7.64-7.58 (m, 2H), 7.54-7.48 (m, 1H), 6.65 (d, 1H$_{major\ rotamer}$), 6.45 (d, 1H$_{minor\ rotamer}$), 4.36-4.27 (m, 1H$_{major\ rotamer}$), 4.17-4.10 (m, 1H$_{minor\ rotamer}$), 3.96-3.89 (m, 1H$_{minor\ rotamer}$), 3.89-3.80 (m, 1H$_{major\ rotamer}$), 2.95 (td, 1H), 2.88-2.79 (m, 1H), 2.31-2.20 (m, 2H), 2.18-2.00 (m, 2H), 1.98-1.75 (m, 4H), 1.69-1.52 (m, 2H).

Example 41

3-(3-chlorophenylethynyl)-3a,4,5,6a-tetrahydropyrrolo[3,2-d]isoxazol-6-yl-(1 methyl-piperidin-4-yl) methanone Intermediate 6e (30 mg, 0.11 mmol) was dissolved in DCM (0.3 mL) under an argon atmosphere. Catalytic DMF was added, then 1-methylpiperidine-4-carboxylic acid (30 mg, 0.21 mmol) and DIPEA (55 µL, 32 mmol). Stirring was continued for 15 mins at room temperature. After 15 min HATU (85 mg, 0.22 mmol) was added and stirring was continued overnight at room temperature. Sodium bicarbonate saturated aq. solution was added (5 mL) and the reaction mixture was extracted with DCM (10 mL, 3×). The organic layer was evaporated to dryness under reduced pressured. The crude product was purified by flash column chromatography on silica using as an eluent DCM:MeOH 9:1 to give 20 mg of solid title compound (51% yield).

MS: [M+H]$^+$=372.3

$^1$H NMR (400 MHz, DMSO-d6) δ 7.78-7.74 (m, 1H), 7.64-7.58 (m, 2H), 7.54-7.47 (m, 1H), 6.64 (d, 1H$_{major\ rotamer}$), 6.45 (d, 1H$_{minor\ rotamer}$), 4.35-4.28 (m, 1H$_{major\ rotamer}$), 4.18-4.11 (m, 1H$_{minor\ rotamer}$), 3.96-3.80 (m, 1H), 3.27-3.00 (m, 3H), 3.00-2.89 (m, 1H), 2.84-2.71 (m, 1H), 2.31-2.23 (m, 1H), 2.21-2.08 (m, 1H), 1.92-1.58 (m, 4H), 1.21-1.11 (m, 1H). Signal from CH$_3$ group covered by DMSO-d$_6$.

Example 42

3-(3-chlorophenylethynyl)-N-(2-methoxyethyl)-N-methyl-3a,4,5,6a-tetrahydropyrrolo[3,2-d]isoxazole-6-carboxamide 3-(3-chlorophenylethynyl)-3a,4,5,6a-tetrahydropyrrolo[3,2-d]isoxazole-6-carbonyl chloride (Intermediate 42a)

Triphosgene (18 mg, 0.06 mmol) was dissolved in dry DCM (0.4 mL) under an argon atmosphere. The reaction mixture was cooled to 0° C. and pyridyne (14 L, 0.18 mmol) was added. After 5 min Intermediate 6e (50 mg, 0.18 mmol) dissolved in dry DCM was added slowly. The reaction mixture was warmed up to room temperature. Stirring was continued for 2 hours at room temperature. The reaction was quenched with 1M HCl (0.35 mL), extracted 5× with DCM (10 mL), and washed with a saturated aq. solution of NaHCO$_3$ (5 mL). The organic layer was dried over Na$_2$SO$_4$, concentrated and dried under reduced pressure to give 73 mg of crude product. The crude product was purified by flash column chromatography using EtOAc:DCM 3:1 as an eluent. 35 mg of a yellow thick oil was obtained. The product was used immediately in the next step without further purification.

3-(3-chlorophenylethynyl)-N-(2-methoxyethyl)-N-methyl-3a,4,5,6a-tetrahydropyrrolo[3,2-d]isoxazole-6-carboxamide Intermediate 42a (35 mg, 11 mmol) was dissolved in DCM (0.6 mL) under an argon atmosphere. The reaction mixture was cooled to 0° C. and triethylamine (32 µL, 0.23 mmol) followed by (2-methoxyethyl)methylamine (25 µL, 0.23 mmol) were added. Stirring was continued for 2 hours at room temperature. Water was added (5 mL) and the reaction mixture was extracted with DCM (10 mL, 3×). The organic layer was dried over Na$_2$SO$_4$ and evaporated to dryness under reduced pressure to give 53 mg of crude product. The crude product was purified by flash column chromatography on silica using EtOAc:DCM 3:1 as an eluent. 25 mg of yellow thick oil was obtained (61% yield).

MS: [2M+Na]$^+$=745.3

$^1$H NMR (400 MHz, DMSO-d6) δ 7.75 (t, 1H), 7.64-7.55 (m, 2H), 7.54-7.46 (m, 1H), 6.52 (d, 1H), 4.12 (t, 1H), 3.61-3.39 (m, 4H), 3.31-3.27 (m, 1H), 3.26 (s, 3H), 3.18-3.05 (m, 1H), 2.88 (s, 3H), 2.25-2.01 (m, 2H).

Example 43

3-(3-fluorophenylethynyl)-3a,4,5,6a-tetrahydropyrrolo[3,2-d]isoxazol-6-yl-morpholin-4-yl-methanone tert-butyl-(3-trimethylsilylethynyl)-3a,4,5,6a-tetrahydropyrrolo[3,2-d]isoxazole-6-carboxylate (Intermediate 20b, alternative procedure)

A solution of tert-butyl 2,3-dihydropyrrole-1-carboxylate (500 mg, 2.95 mmol) and 3-trimethylsilylprop-2-ynal oxime (459.06 mg, 3.25 mmol) in MTBE (15 mL) was cooled to 0-5° C. while stirring. Sodium hypochlorite (2.806 mL, 5.91 mmol) was added dropwise keeping the reaction temperature below 20° C. The reaction mixture was stirred at the same temperature for 3 hours; afterwards, it was quenched with Na$_2$SO$_3$ solution; the two phases were separated, the organic layer was washed with water and brine, dried over Na$_2$SO$_4$, filtered and evaporated to dryness in vacuo. The crude residue was purified by automated flash chromatography (Biotage SP1, cartridge type SNAP25) using a gradient from petroleum ether:EtOAc 95:5 to 7:3. Further purification by automated flash chromatography (Isolera Biotage) with a gradient Petroleum Ether:EtOAc from 5:5 to 0:10 afforded 250 mg of the title product. Yield: 27%.

tert-butyvl-3-(3-fluorophenylethynyl)-3a,4,5,6a-tetrahydropyrrolo[3,2-d]isoxazole-6-carboxylate (Intermediate 43a)

The title compound was synthesized using the method reported above for Intermediate 20c, but replacing 2-bromo-6-methylpyridyne with 1-fluoro-3-iodo-benzene. After the usual work-up procedure the residue was purified by automated flash chromatography (Isolera Biotage; gradient Petroleum Ether:EtOAc from 95:5 to 7:3) to give the title compound. Yield: 76%.
MS: [M+H]$^+$=331.65

3-(3-fluorophenylethynyl)-4,5,6,6a-tetrahydropyrrolo[3,2-d]isoxazole (Intermediate 43b)

The title compound was synthesized using the method reported above for Intermediate 6e, but replacing Intermediate 6d with Intermediate 43a. After the usual work-up procedure the residue was used for the next step without further purification. Yield: 95% (crude product).
MS: [M+H]$^+$=231.54

3-(3-fluorophenylethynyl)-3a,4,5,6a-tetrahydropyrrolo[3,2-d]isoxazol-6-yl-morpholin-4-yl-methanone To a solution of Intermediate 43b (50 mg, 0.21 mmol) in CH$_2$Cl$_2$ (6 mL) was added TEA (56 µL, 0.43 mmol) and then, dropwise, morpholine-4-carbonyl chloride (38.1 µL, 0.32 mmol). The reaction was heated at 50° C. for 4 h. The reaction mixture was then poured into water, the organic layer was separated, dried over Na$_2$SO$_4$ and evaporated to dryness in vacuo. The crude product was purified by flash chromatography (Isolera® Biotage) eluting with a gradient petroleum ether:ethyl acetate 8:2 to 2:8 affording the title compound as a white solid (0.31 g, 41% yield).
MS: [M+H]$^+$=344.54
$^1$H NMR (400 MHz, DMSO-d6) ppm 7.45-7.58 (m, 3H) 7.34-7.43 (m, 1H) 6.54 (d, 1H) 4.10-4.19 (m, 1H) 3.51-3.69 (m, 5H) 3.30-3.38 (m, 2H) 3.19-3.28 (m, 2H) 3.12 (td, 1H) 2.05-2.25 (m, 2H)

Example 44

3-(3-fluorophenylethynyl)-3a,4,5,6a-tetrahydropyrrolo[3,2-d]isoxazol-6-yl-(pyrrolidin-1-yl)methanone The title compound was synthesized using the method reported above for Example 43, but replacing 4-pyrrolidine carbonyl chloride for morpholine-4-carbonyl chloride. After the usual work-up procedure the residue was purified by flash chromatography (Isolera® Biotage) eluting with a gradient petroleum ether:ethyl acetate 8:2 to 2:8 affording the title compound as a white solid (0.20 g, 28% yield).
MS: [M+H]$^+$=328.54
$^1$H NMR (400 MHz, DMSO-d6) ppm 7.45-7.58 (m, 3H) 7.29-7.44 (m, 1H) 6.54 (d, 1H) 4.19 (dd, 1H) 3.68 (dd, 1H) 3.35-3.46 (m, 2H) 3.23-3.28 (m, 2H) 3.11 (td, 1H) 2.04-2.28 (m, 2H) 1.59-1.93 (m, 4H)

Example 45

3-phenylethynyl-3a,4,5,6a-tetrahydropyrrolo[3,2-d]isoxazol-6-yl-(morpholin-4-yl)methanone tert-butyl-3-(2-phenylethynyl)-3a,4,5,6a-tetrahydropyrrolo[3,2-d]isoxazole-6-carboxylate (Intermediate 45a)

The title compound was synthesized using the method reported above for Intermediate 20c, but replacing 2-bromo-6-methylpyridyne with iodobenzene. After the usual work-up procedure the residue was purified by means of automated flash chromatography (Isolera-Biotage; gradient Petroleum Ether:EtOAc from 95:5 to 7:3) to give the title compound.
Yield: 59%.
MS: [M+H]$^+$=313.51

3-(2-phenylethynyl)-4,5,6,6a-tetrahydropyrrolo[3,2-d]isoxazole (Intermediate 45b)

The title compound was synthesized using the method reported above for Intermediate 6e, but replacing Intermediate 6d with Intermediate 45a. After the usual work-up procedure the residue was used for the next step without further purification Yield: 98% (crude product).
MS: [M+H]$^+$=213.54

3-phenylethynyl-3a,4,5,6a-tetrahydropyrrolo[3,2-d]isoxazol-6-yl-(morpholin-4-yl)methanone The title compound was synthesized using the method reported above for Example 43, but replacing Intermediate 43b with Intermediate 45b. After the usual work-up procedure the residue was purified by flash chromatography (Isolera® Biotage) eluting with a gradient petroleum ether:ethyl acetate 8:2 to 2:8 affording the title compound as a white solid (0.23 g, 25% yield).
MS: [M+H]$^+$=326.55
$^1$H NMR (400 MHz, DMSO-d6) ppm 7.59-7.66 (m, 2H) 7.43-7.56 (m, 3H) 6.53 (d, 1H) 4.13 (dd, 1H) 3.52-3.69 (m, 5H) 3.33-3.41 (m, 2H) 3.19-3.28 (m, 2H) 3.13 (td, 1H) 2.05-2.24 (m, 2H)

Example 46

3-(3-bromophenylethynyl)-3a,4,5,6a-tetrahydropyrrolo[3,2-d]isoxazol-6-yl-(pyrrolidin-1-yl)methanone tert-Butyl-3-(3-bromophenylethynyl)-3a,4,5,6a-tetrahydropyrrolo[3,2-d]isoxazole-6-carboxylate (Intermediate 46a)

The title compound was synthesized using the method reported above for Intermediate 20c, but replacing 2-bromo-6-methylpyridyne with 1-bromo-3-iodo-benzene. After the usual work-up procedure the residue was purified by means of automated flash chromatography (Isolera-Biotage; gradient Petroleum Ether:EtOAc from 9:1 to 6:4) to give the title compound. Yield: 42%.
MS: [M+H]$^+$=392.66

3-(3-bromophenylethynyl)-4,5,6,6a-tetrahydropyrrolo[3,2-d]isoxazole (Intermediate 46b)

The title compound was synthesized using the method reported above for Intermediate 6e, but replacing Intermediate 6d with Intermediate 46a. After the usual work-up procedure the residue was used for the next step without further purification Yield: 89% (crude product).

MS: [M+H]$^+$=292.78

3-(3-bromophenylethynyl)-3a,4,5,6a-tetrahydropyrrolo[3,2-d]isoxazol-6-yl-(pyrrolidin-1-yl)methanone The title compound was synthesized using the method reported above for Example 43, but replacing Intermediate 43b with Intermediate 46b and 4-pyrrolidine carbonyl chloride for morpholine-4-carbonyl chloride. After the usual work-up procedure the residue was purified by flash chromatography (Isolera® Biotage) eluting with a gradient petroleum ether:ethyl acetate 8:2 to 2:8 affording the title compound as a white solid (0.20 g, 19% yield).

MS: [M+H]$^+$=389.71

$^1$H NMR (400 MHz, DMSO-d6) ppm 7.87 (m, 1H), 7.72 (m, 1H), 7.64 (m, 1H), 7.39-7.48 (m, 1H), 6.54 (d, 1H), 4.07-4.18 (m, 1H), 3.60-3.72 (m, 1H), 3.34-3.44 (m, 2H), 3.31 (d, 2H), 3.11 (m, 1H), 2.03-2.30 (m, 2H), 1.64-1.94 (m, 4H).

All references cited in this application are incorporated by reference in their entirety.

The invention claimed is:

1. A compound of Formula I;

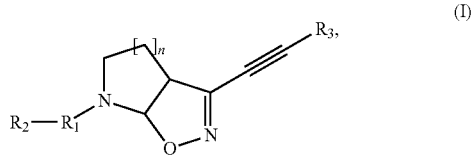 (I)

or an enantiomer, diastereomer, N-oxide, or a pharmaceutically acceptable salt thereof, wherein:

$R_1$ is chosen from the group consisting of an alkyl group, an optionally substituted mono-, bi- or tricyclic $C_1$-$C_{13}$ heterocyclic group containing 1 to 5 heteroatoms selected from N, O, and S; an optionally substituted mono-, bi- or tricyclic $C_6$-$C_{14}$ aryl group, an optionally substituted $C_3$-$C_6$ cycloalkyl group, or an optionally substituted $C_3$-$C_6$ cycloalkenyl group; CO, CS, CH, CH2 and an SO2 group optionally substituted by one or more $R_2$ groups or substituents;

$R_2$ is chosen from the group consisting of an optionally substituted mono- or bicyclic $C_1$-$C_9$ heterocyclic group containing from 1 to 3 heteroatoms selected from nitrogen, oxygen and sulfur, an optionally substituted mono-, bi- or tricyclic $C_6$-$C_{14}$ aryl group, or an optionally substituted group chosen from alkyl, cycloalkyl, alkoxy, cycloalkyloxy, aryloxy, heteroaryloxy, alkylthio, amino, N-alkylamino, N,N-dialkylamino, and N-alkyl-N-alkoxyamino;

$R_3$ is chosen from the group consisting of an optionally substituted alkyl group, an optionally substituted mono-, bi- or tricyclic $C_1$-$C_{13}$ heterocyclic group containing 1 to 5 heteroatoms selected from N, O, and S; an optionally substituted mono-, bi- or tricyclic $C_6$-$C_{14}$ aryl group, an optionally substituted $C_3$-$C_6$ cycloalkyl group, and an optionally substituted $C_3$-$C_6$ cycloalkenyl group; and n is 1-3.

2. The compound according to claim 1, wherein optional substituents being independently selected from the group consisting of halogen atoms and $C_1$-$C_6$ alkyl, $C_1$-$C_6$ alkoxy, hydroxy, mercapto, nitro, cyano, oxo, halo($C_1$-$C_6$) alkyl, halo($C_1$-$C_6$)alkoxy, $C_1$-$C_6$ alkylthio, $C_1$-$C_6$ alkylsulphonyl, $C_1$-$C_6$ alkylcarbonyl, sulphamoyl, $C_1$-$C_6$ alkylsulphamoyl, di($C_1$-$C_6$)alkylsulphamoyl, ($C_1$-$C_6$) alkoxycarbonyl and ($C_1$-$C_6$)alkylcarbonyl($C_1$-$C_6$)alkyl groups, and from groups of the formulae —NR*R*, —C(=O)—NR*R*, -A, —O-A, —C(=O)-A, —(CH2)q-A, —NR-A, —C(=O)—NR-A, —NR**C(=O)-A and —O—C(=O)-A wherein each R* independently represents a hydrogen atom or a $C_1$-$C_6$ alkyl, $C_1$-$C_6$ alkoxy, $C_1$-$C_6$ alkylcarbonyl, phenyl or benzyl group, R** represents a hydrogen atom or a $C_1$-$C_6$ alkyl group, q is an integer from 1 to 6 and A represents a phenyl group or a $C_1$-$C_8$ heterocyclic group containing from 1 to 3 heteroatoms selected from N, O and S; a $C_1$-$C_6$ cycloalkyl group; each group A being optionally substituted with from 1 to 3 groups independently selected from halo, hydroxy, cyano, nitro and $C_1$-$C_6$ alkyl, preferably wherein the optional substituents are independently selected from the groups consisting of halogen atoms and $C_1$-$C_6$ alkyl groups.

3. The compound according to claim 1, wherein n=1.

4. The compound according to claim 1, wherein $R_1$ is a CO group.

5. The compound according to claim 1, wherein $R_2$ is an optionally substituted mono- or bicyclic $C_1$-$C_9$ heterocyclic group containing from 1 to 3 heteroatoms selected from nitrogen, oxygen and sulfur, or an optionally substituted group chosen from cycloalkyl, alkoxy, cycloalkyloxy, aryloxy, heteroaryloxy, amino, N-alkylamino, N,N-dialkylamino, or N-alkyl-N-alkoxy.

6. The compound according to claim 5, wherein $R_2$ has the formula:

where R4 is chosen from the group consisting of a $C_1$-$C_{10}$ linear or branched alkyl group, a $C_1$-$C_{10}$ cycloalkyl group and a $C_1$-$C_{10}$ heterocyclic group containing at least one heteroatom selected from N or O.

7. The compound according to claim 5 wherein $R_2$ is chosen from the group consisting of a saturated or unsaturated, optionally substituted, five or six membered homocyclic group and heterocyclic group containing at least one heteroatom selected from N or O.

8. The compound according to claim 5 wherein $R_2$ has the formula:

where R5 is chosen from the group consisting of a $C_1$-$C_{10}$ linear or branched alkyl, alkoxy group and hydrogen; R6 is a $C_1$-$C_{10}$ linear or branched alkyl or alkoxy group, $R_5$ and $R_6$ being the same or different; or wherein $R_5$ and $R_6$ together with the nitrogen atom form a five or six membered heterocyclic ring.

9. The compound according to claim 1, wherein $R_3$ is chosen from the group consisting of an optionally substituted mono-, bi- or tricyclic $C_6$-$C_{14}$ aryl group, an optionally substituted, five or six membered heterocyclic group containing at least one heteroatom selected from N or O, an optionally substituted $C_3$-$C_6$ cycloalkyl group, and an optionally substituted $C_3$-$C_6$ cycloalkenyl group.

10. The compound according to claim 9, wherein $R_3$ is a phenyl or pyridyl group, said optional substituents being selected from a $C_1$-$C_{10}$ alkyl group or a halide group.

11. The compound according to claim 1, wherein $R_1$ represents an optionally substituted CO group, $R_2$ is absent, $R_3$ represents a phenyl, 3-bromophenyl, 3-chlorophenyl, 3-fluorophenyl, 3-methylphenyl or a 6-methyl-2-pyridyl group and n is 1.
12. A compound according to claim 1 selected from the group consisting of:
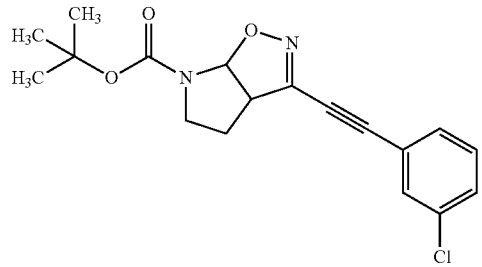
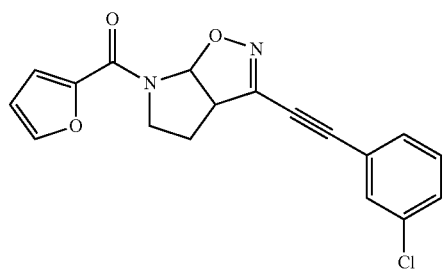
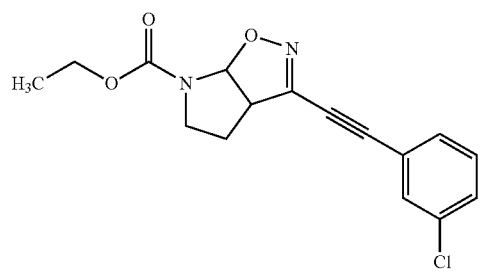
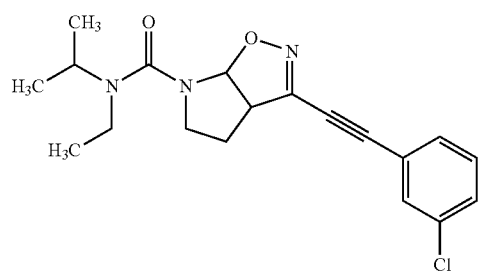
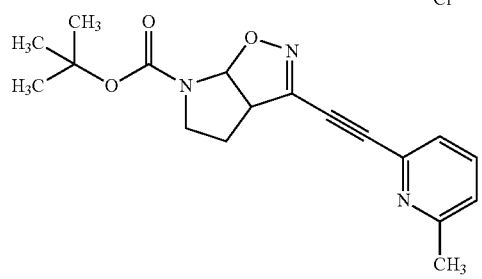
-continued
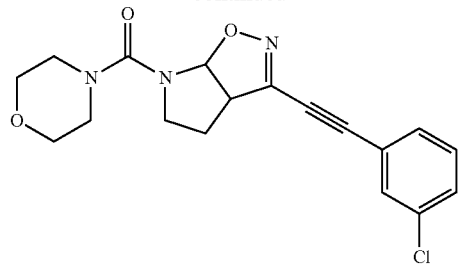
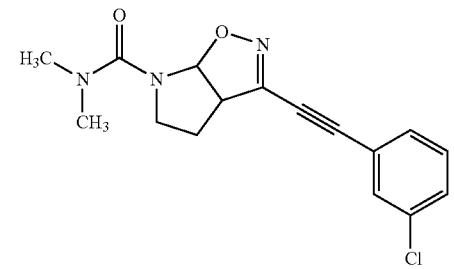
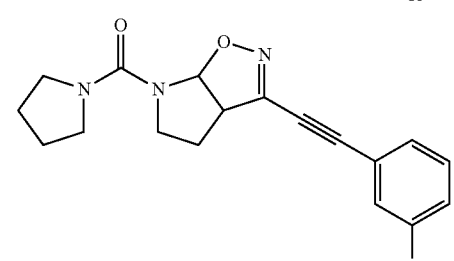
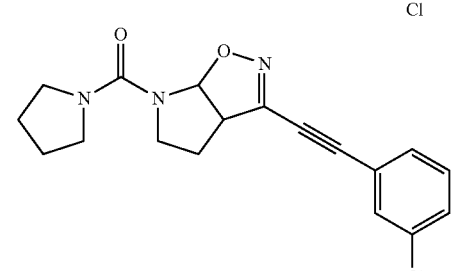
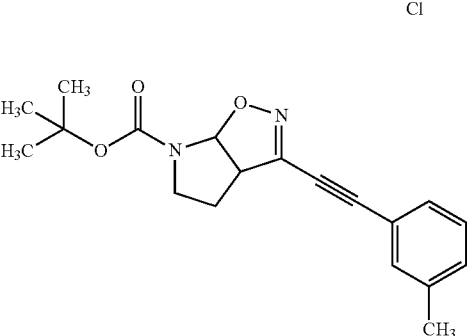
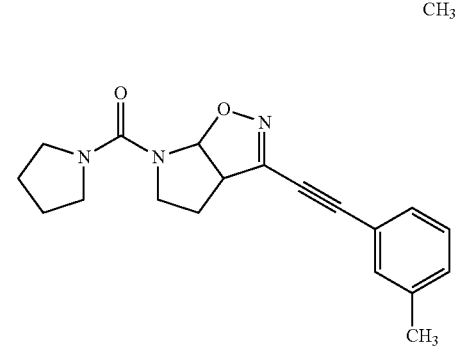

59
-continued
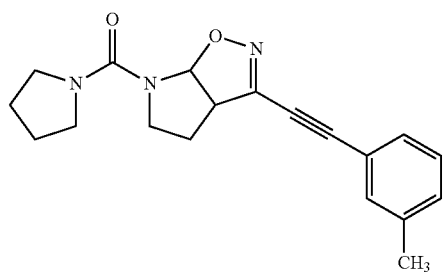
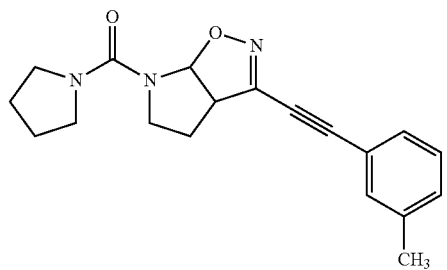
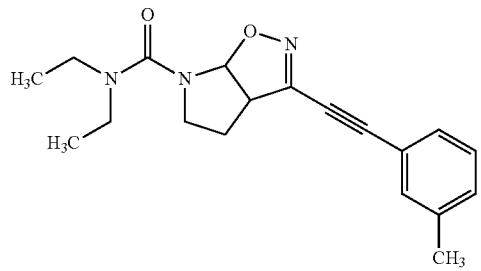
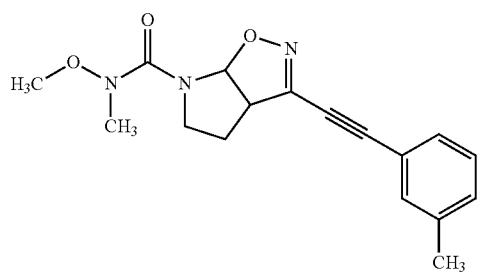
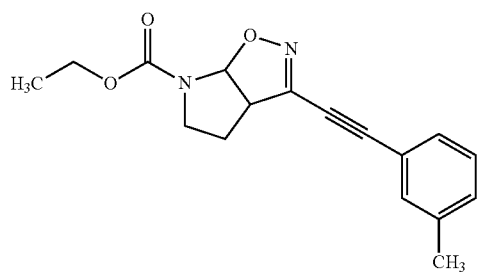
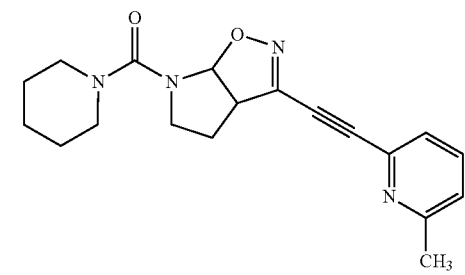
60
-continued
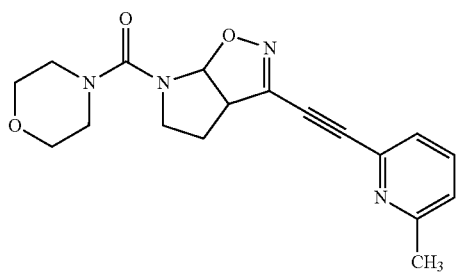
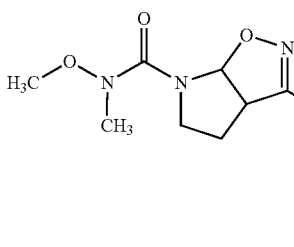
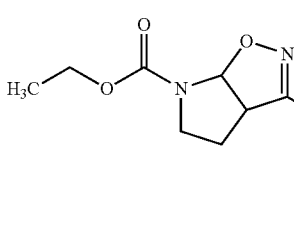
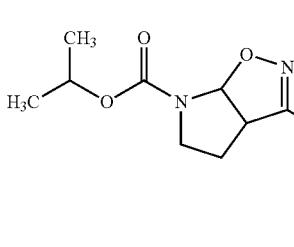
or a pharmaceutically acceptable salt thereof.
13. A compound according to claim 1 selected from the group consisting of:
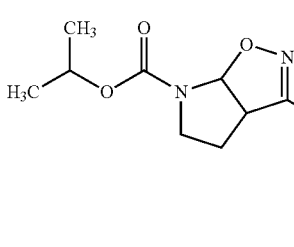
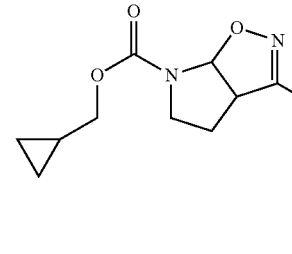

61
-continued
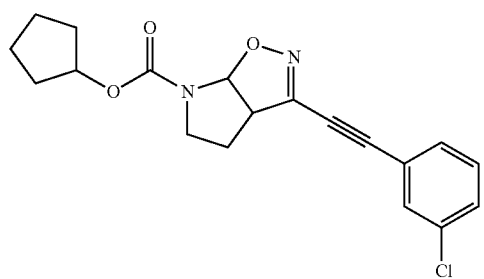
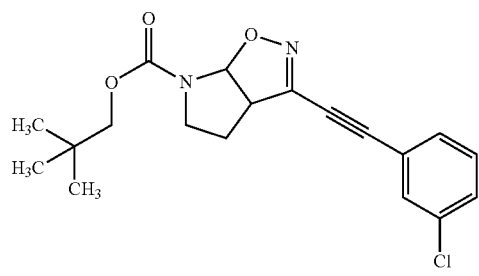
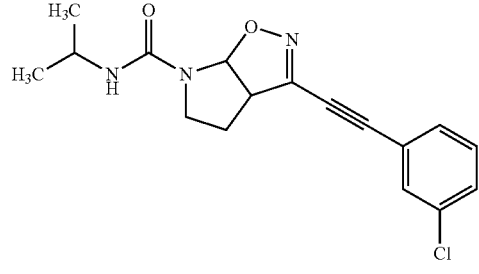
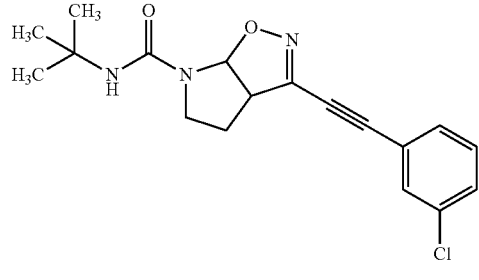
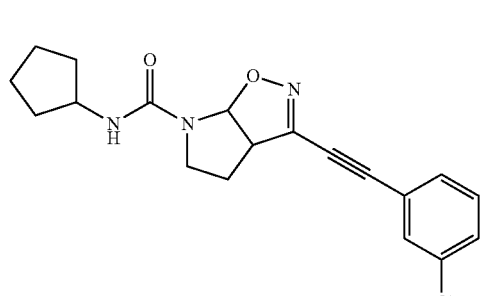
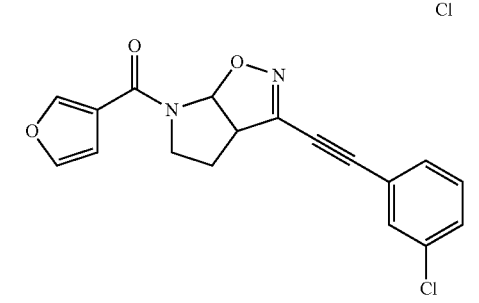
62
-continued
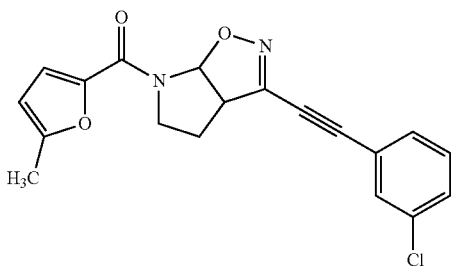
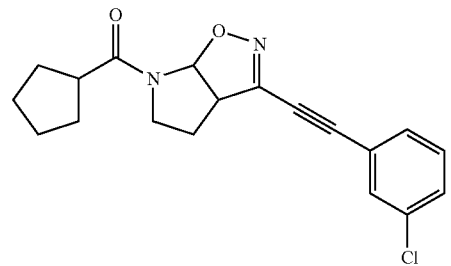
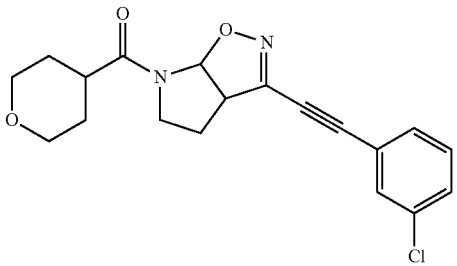
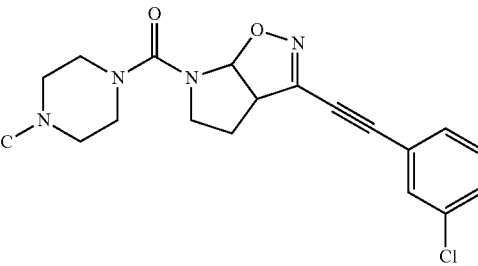
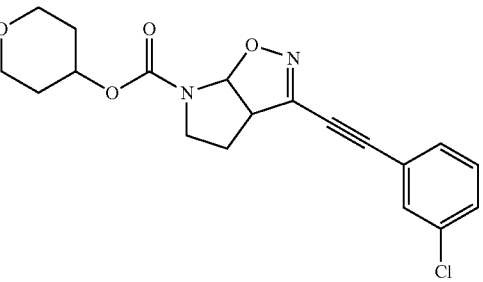
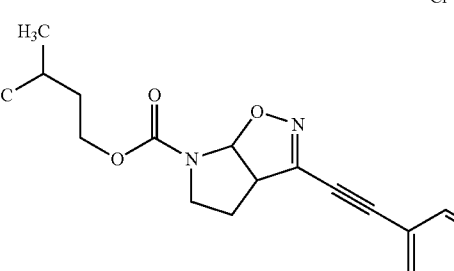

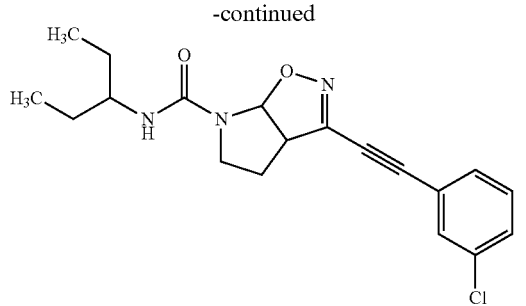
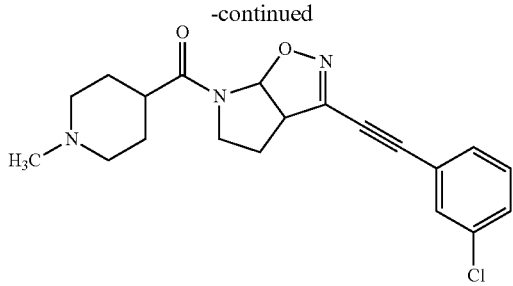
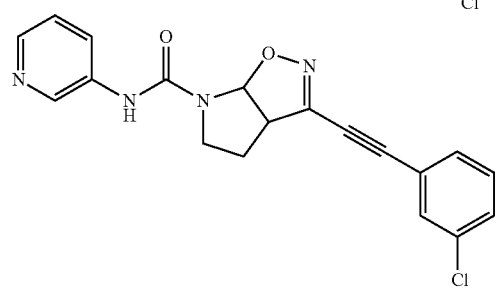
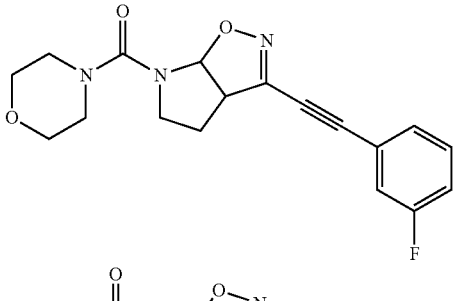
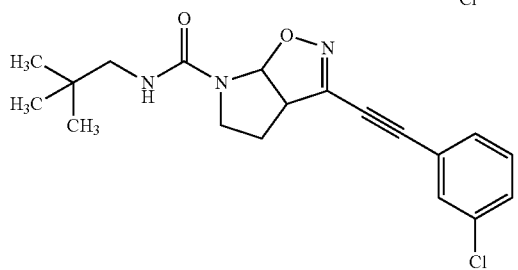
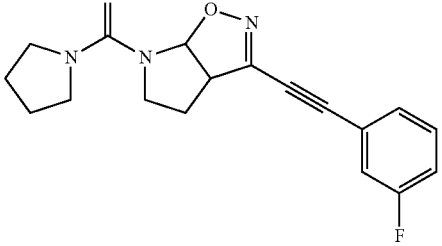
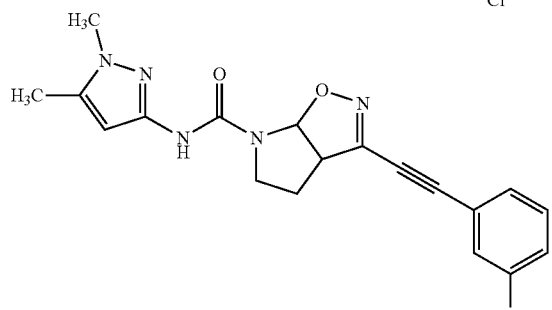
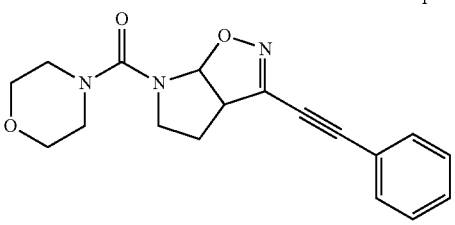 and
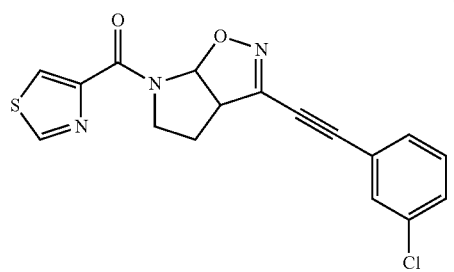
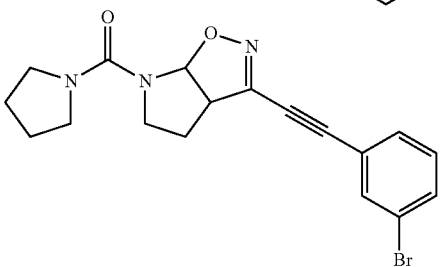
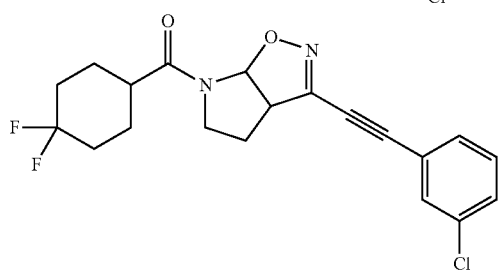
or a pharmaceutically acceptable salt thereof.
14. A pharmaceutical composition comprising a compound according to claim 1.
* * * * *